US011772305B2

(12) United States Patent
Mochizuki et al.

(10) Patent No.: US 11,772,305 B2
(45) Date of Patent: *Oct. 3, 2023

(54) PRODUCTION METHOD OF MOLD HAVING RECESSED PATTERN IN RECESSED STEP PORTION

(71) Applicant: FUJIFILM Corporation, Tokyo (JP)

(72) Inventors: Aya Mochizuki, Kanagawa (JP); Satoshi Chai, Kanagawa (JP); Toshihiro Usa, Kanagawa (JP); Kozue Ikeda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,643

(22) Filed: Oct. 26, 2022

(65) Prior Publication Data

US 2023/0075192 A1 Mar. 9, 2023

Related U.S. Application Data

(62) Division of application No. 16/807,181, filed on Mar. 3, 2020, now Pat. No. 11,534,943.

(30) Foreign Application Priority Data

Mar. 5, 2019 (JP) .................................. 2019-039492

(51) Int. Cl.
  *B29C 33/38* (2006.01)
  *A61M 37/00* (2006.01)
  *B29C 33/40* (2006.01)
  *B29C 33/42* (2006.01)

(52) U.S. Cl.
  CPC ..... *B29C 33/3857* (2013.01); *A61M 37/0015* (2013.01); *B29C 33/3842* (2013.01);
  (Continued)

(58) Field of Classification Search
  CPC ............ B29C 33/3842; B29C 33/3857; B29C 33/3878; B29C 33/40; B29C 33/424;
  (Continued)

(56) References Cited

U.S. PATENT DOCUMENTS 11,534,943 B2 * 12/2022 Mochizuki .......... B29C 33/3857
2012/0078189 A1 * 3/2012 Ogawa .................... B29C 39/42
604/173

(Continued)

FOREIGN PATENT DOCUMENTS

EP   2011083993    4/2011
EP   3108924       12/2016
(Continued)

OTHER PUBLICATIONS

"Office Action of U.S. Counterpart Application, U.S. Appl. No. 16/807,181", dated Mar. 14, 2022, p. 1-p. 30.
(Continued)

*Primary Examiner* — Jerzi H Moreno Hernandez
(74) *Attorney, Agent, or Firm* — JCIPRNET

(57) ABSTRACT

A production method of a mold having a recessed pattern includes: a plate precursor preparation step of preparing a plate precursor having a pedestal on which a protruding pattern is disposed; a resin plate preparation step of preparing a thermoplastic resin plate having a recessed step portion; and a resin plate precursor production step of producing a thermoplastic resin plate precursor. The plate precursor comprises a substrate having a larger area than the pedestal in a plan view on a side opposite to a surface of the pedestal on which the protruding pattern is disposed. An edge portion where a side surface of the pedestal and the substrate are in contact with each other has a through-hole penetrating the substrate along the side surface of the pedestal.

11 Claims, 23 Drawing Sheets

(52) U.S. Cl.
CPC ..... *B29C 33/40* (2013.01); *A61M 2037/0053* (2013.01); *B29C 33/424* (2013.01); *B29C 2033/426* (2013.01)

(58) Field of Classification Search
CPC ............. B29C 33/426; A61M 37/0015; A61M 2037/0053; A61M 2037/0046
See application file for complete search history.

(56) References Cited

U.S. PATENT DOCUMENTS

| | | | |
|---|---|---|---|
| 2017/0101242 A1 | 4/2017 | Yamada et al. | |
| 2017/0327963 A1 | 11/2017 | Chai et al. | |
| 2017/0361082 A1* | 12/2017 | Okano | B29C 39/025 |
| 2018/0215078 A1* | 8/2018 | Ogawa | B29C 33/3857 |
| 2018/0222088 A1* | 8/2018 | Ogawa | B29C 39/02 |
| 2018/0250851 A1 | 9/2018 | Ogawa et al. | |
| 2020/0114547 A1* | 4/2020 | Ori | B29C 33/3892 |

FOREIGN PATENT DOCUMENTS

| | | | |
|---|---|---|---|
| EP | 2017202242 | 11/2017 | |
| EP | 3357862 | 8/2018 | |
| JP | 2014004077 | 1/2014 | |
| JP | 2015231476 | 12/2015 | |
| WO | 2015147030 | 10/2015 | |
| WO | WO-2017056894 A1 * | 4/2017 | ......... B29C 33/3857 |
| WO | WO-2019225288 A1 * | 11/2019 | |

OTHER PUBLICATIONS

"Office Action of Japan Counterpart Application, Application No. 2019-039492" with English translation thereof, dated Oct. 27, 2021, p. 1-p. 9.

"Search Report of Europe Counterpart Application, Application No. 20160513.6", dated Jun. 9, 2020, p. 1-p. 6.

"Office Action of U.S. Counterpart Application, U.S. Appl. No. 16/807,181", dated Aug. 30, 2022, p. 1-p. 5.

* cited by examiner

PRODUCTION METHOD OF MOLD HAVING RECESSED PATTERN IN RECESSED STEP PORTION

CROSS-REFERENCE TO RELATED APPLICATION

This application is a divisional application of and claims the priority benefit of a prior application Ser. No. 16/807,181, filed on Mar. 3, 2020. The prior application Ser. No. 16/807,181 claims priority under 35 U.S.C. § 119(a) to Japanese Patent Application No. 2019-039492 filed on Mar. 5, 2019, which is hereby expressly incorporated by reference, in its entirety, into the present application.

BACKGROUND OF THE INVENTION

1. Field of the Invention

The present invention relates to a production method of a mold having a recessed pattern in a recessed step portion and a manufacturing method of a pattern sheet, and particularly to a production method of a mold for manufacturing a pattern sheet by shape transfer and a manufacturing method of a pattern sheet using the mold.

2. Description of the Related Art

In recent years, as a novel dosage form capable of injecting drugs such as insulin, vaccines, and human growth hormone (hGH) into the skin without pain, a microneedle array has been known. The microneedle array is an array of microneedles (also referred to as fine needles or small needles) which contain drugs and are biodegradable. By attaching this microneedle array to the skin, each microneedle pierces the skin, and these microneedles are absorbed in the skin such that the drugs contained in each microneedle can be administered into the skin. Microneedle arrays are also called percutaneous absorption sheets.

In order to produce a molded product having a fine protruding pattern such as a microneedle array as described above, a resin mold having an inverted shape is formed from a plate precursor having the fine protruding pattern, and a molded product is produced from the mold. There is a demand for improving the productivity of molded products having such fine patterns, and various proposals have been made.

For example, in JP2011-083993A, it is described that a plate precursor having a fine protruding pattern is pressed against a thermoplastic resin plate to transfer the protruding pattern, whereby a thermoplastic resin plate precursor having an inverted pattern is produced. Furthermore, an electroform having the protruding pattern is produced from the thermoplastic resin plate precursor. Moreover, a mold having the inverted pattern is produced from the electroform. JP2015-231476A describes a mold which is provided with a step in order to prevent a resin solution forming a pattern sheet from flowing out of the mold and flowing beyond a target location in a case where the pattern sheet is formed, and a plate precursor for forming the step in the mold.

WO2017/056894A describes that a thermoplastic resin sheet having a recessed pattern is produced by pressing a plate precursor having a heated protruding pattern against the thermoplastic resin sheet having a depression formed therein, and a mold having the recessed pattern for manufacturing a pattern sheet from an electroform is manufactured. JP2017-202242A describes a mold is produced using a plate precursor having an inclined portion whose thickness gradually increases from the inner side toward the outer side of the plate precursor, and a volume raised portion corresponding to the total volume of a pressed protruding portion is formed in an inverted tapered shape.

SUMMARY OF THE INVENTION

However, in the methods described in JP2011-083993A, JP2015-231476A, and WO2017/056894A, the pattern of the mold is transferred to the thermoplastic resin plate while pressing a flat surface of the mold against the thermoplastic resin plate, so that the resin corresponding to the volume of the pattern of the mold in the pattern surface is raised. There is a problem that a steep step is formed at the end portion of the raised resin and has an adverse effect on the subsequent electroforming and molding. Furthermore, in a case where a recessed step is provided in the periphery of the inverted pattern of the thermoplastic resin plate precursor, a gap is formed between the end portion of the raised resin and the recessed step, and there is concern that this gap may also have a greater adverse effect on the electroforming and molding.

In addition, although JP2017-202242A describes that the mold is produced in consideration of the raised portion of the resin, a configuration for manufacturing a mold in which a recessed pattern is formed in a recessed step portion capable of preventing a liquid material from flowing in a case where a pattern sheet is manufactured after the mold is produced is not described.

Moreover, in a case where the recessed pattern is formed at the bottom surface of the recessed step portion without considering the size of the recessed step portion, the raised portion of the resin is formed inside the recessed step portion. Therefore, there is concern that the shape of the recessed step portion having the recessed pattern may not become stable and have an adverse effect on the subsequent electroforming and molding.

The present invention has been made in view of such circumstances, and an object thereof is to provide a production method of a mold having a recessed pattern in a recessed step portion, in which a portion of a resin raised in a case where a recessed pattern is formed in a recessed step portion is formed outside the recessed step portion such that failure in subsequent processes such as production of an electroform and mold forming can be minimized, and a manufacturing method of a pattern sheet.

In order to achieve the object of the present invention, a production method of a mold having a recessed pattern in a recessed step portion according to the present invention, comprises: a plate precursor preparation step of preparing a plate precursor having a pedestal on which a protruding pattern formed by a plurality of protruding portions is disposed; a resin plate preparation step of preparing a thermoplastic resin plate in which a recessed step portion having a bottom surface and a wall surface is formed on a flat surface thereof, the recessed step portion having a volume equal to or less than a total volume of the protruding pattern and the pedestal; and a resin plate precursor production step of producing a thermoplastic resin plate precursor, the resin plate precursor production step including a positioning step of positioning the protruding pattern of the plate precursor and a center position of the recessed step portion by moving the plate precursor and the thermoplastic resin plate relative to each other, and a recessed pattern forming step of forming a recessed pattern having an inverted shape of the protruding pattern on the thermoplastic resin plate by pressing the protruding pattern of the heated plate precursor and the pedestal against the bottom surface of the recessed step portion, thereafter cooling the plate precursor, and separating the plate precursor from the thermoplastic resin plate.

In order to achieve the object of the present invention, a manufacturing method of a pattern sheet according to the present invention comprises: a step of producing a mold having a recessed pattern in a recessed step portion by the production method of a mold having a recessed pattern in a recessed step portion described above; a step of supplying a liquid material to the recessed step portion of the mold to fill the recessed pattern of the mold with the liquid material; a step of solidifying the liquid material to form a pattern sheet having a protruding pattern; and a releasing step of releasing the pattern sheet from the mold.

According to the present invention, since the recessed pattern can be formed in the recessed step portion that prevents a liquid from flowing, and the recessed step portion has a volume equal to or less than the total volume of the protruding pattern and the pedestal, the resin of the thermoplastic resin plate pushed away by the protruding portion and the pedestal in a case where the thermoplastic resin plate precursor is produced can be taken out of the recessed step portion. Accordingly, the bottom surface of the recessed step portion in which the recessed pattern is formed can be formed flat. Therefore, it is possible to minimize failure in processes in the production of the die after the production of the thermoplastic resin plate precursor, the production of the mold, and the manufacturing of the pattern sheet using the mold.

DESCRIPTION OF THE PREFERRED EMBODIMENTS

Figure 1:
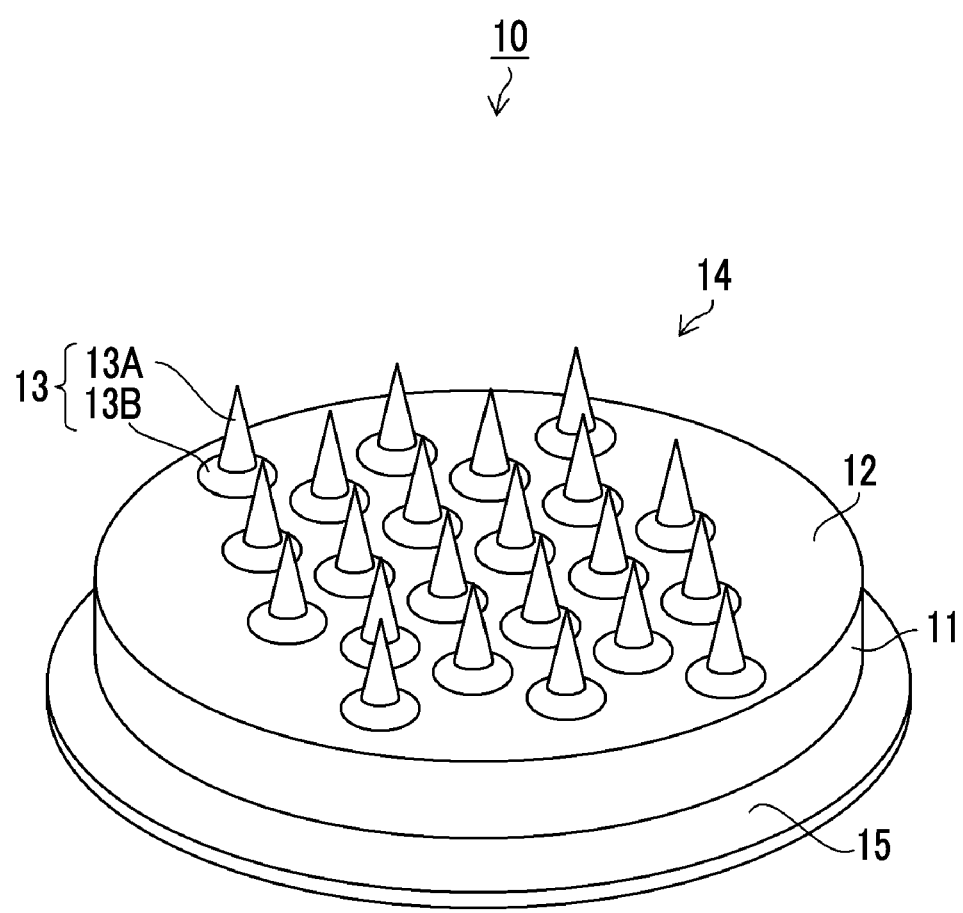
FIG. 1 is a perspective view illustrating an example of a plate precursor.

Hereinafter, a production method of a mold having a recessed pattern in a recessed step portion and a manufacturing method of a pattern sheet according to the present invention will be described with reference to the accompanying drawings. The present invention is described by the following preferred embodiments. Modifications can be made by a number of techniques without departing from the scope of the invention. Therefore, all modifications within the scope of the present invention are included in the appended claims.

Here, in the figures, like elements having similar functions are denoted by like reference numerals. In addition, in this specification, in a case where a numerical value range is expressed using "to", the numerical value range includes the numerical values of the upper limit and the lower limit indicated by "to".

Production Method of Mold

An embodiment of the present invention will be described with reference to the drawings. A production method of a mold having a recessed pattern in a recessed step portion includes: a plate precursor preparation step of preparing a plate precursor having a pedestal on which a protruding pattern formed by a plurality of protruding portions is disposed; a resin plate preparation step of preparing a thermoplastic resin plate in which a recessed step portion having a bottom surface and a wall surface is formed on a flat surface thereof, the recessed step portion having a volume equal to or less than a total volume of the protruding pattern and the pedestal; and a resin plate precursor production step of producing a thermoplastic resin plate precursor, the resin plate precursor production step including a positioning step of positioning the protruding pattern of the plate precursor and a center position of the recessed step portion by moving the plate precursor and the thermoplastic resin plate relative to each other, and a recessed pattern forming step of forming a recessed pattern having an inverted shape of the protruding pattern on the thermoplastic resin plate by pressing the protruding pattern of the heated plate precursor and the pedestal against the bottom surface of the recessed step portion, thereafter cooling the plate precursor, and separating the plate precursor from the thermoplastic resin plate.

In the plate precursor preparation step, the plate precursor is prepared. As illustrated in FIG. 1, a plate precursor 10 has a pedestal 11, a plurality of protruding portions 13 formed on one main surface 12 of the pedestal 11, and a substrate 15 provided on a side opposite to the main surface 12 of the pedestal 11. The substrate 15 is disposed so as to overlap the pedestal 11 in a plan view, and has an area larger than the area of the pedestal 11. The protruding portion 13 is formed by a frustum portion 13B and a tapered needle portion 13A in a direction away from the main surface 12. The frustum portion 13B includes a pyramidal frustum, a conical frustum, and the like. In addition, another frustum portion may be included between the frustum portion 13B and the needle portion 13A.

A protruding pattern 14 is configured by arranging a plurality of the protruding portions 13 on the main surface 12. The main surface 12 corresponds to the surface on which the protruding pattern 14 is disposed. The protruding pattern 14 of the plate precursor 10 has a protruding pattern basically the same as a pattern sheet, such as a microneedle, having a protruding pattern to be produced. In the embodiment, the protruding pattern 14 is configured by arranging the plurality of protruding portions 13 in a circular shape. However, the number of the protruding portions 13 and the positions of the protruding portions 13 in the arrangement are not limited. By arranging the plurality of protruding portions 13 in a matrix, the protruding pattern 14 can be configured. The main surface 12 may be a complete flat surface or a flat surface at first glance.

For example, the protruding portion 13 is preferably set to a height of 0.1 mm to 2 mm from the main surface 12 of the plate precursor 10. The interval between adjacent protruding portions 13 is preferably 0.3 mm to 2 mm. The aspect ratio of the protruding portion 13 (the height of the protruding portion/the width of the bottom surface of the protruding portion) is preferably 1 to 5.

The ratio between the height of the needle portion 13A and the height of the frustum portion 13B (the height of the needle portion 13A/the height of the frustum portion 13B) is preferably 1 to 10. The angle formed between the side surface of the frustum portion 13B and the main surface 12 is preferably 10° to 60°. For example, the pedestal 11 can have a cylindrical shape having a diameter of 5 mm to 30 mm and a height of 0.2 mm to 2 mm. However, the shape of the pedestal 11 is not limited to the cylindrical shape, and may be a rectangular parallelepiped shape. The substrate 15 may be formed integrally with the surface opposite to the main surface 12 of the pedestal 11 instead of being a member different from the pedestal 11. In this case, the volume of the substrate 15 is not included in the volume of the pedestal 11.

For example, the plate precursor 10 having the protruding pattern 14 is produced by machining a metal substrate, which is to become the plate precursor 10, using a cutting tool such as a diamond tool. As the metal substrate, stainless steel, an aluminum alloy, Ni, or the like can be used.

Figure 2:
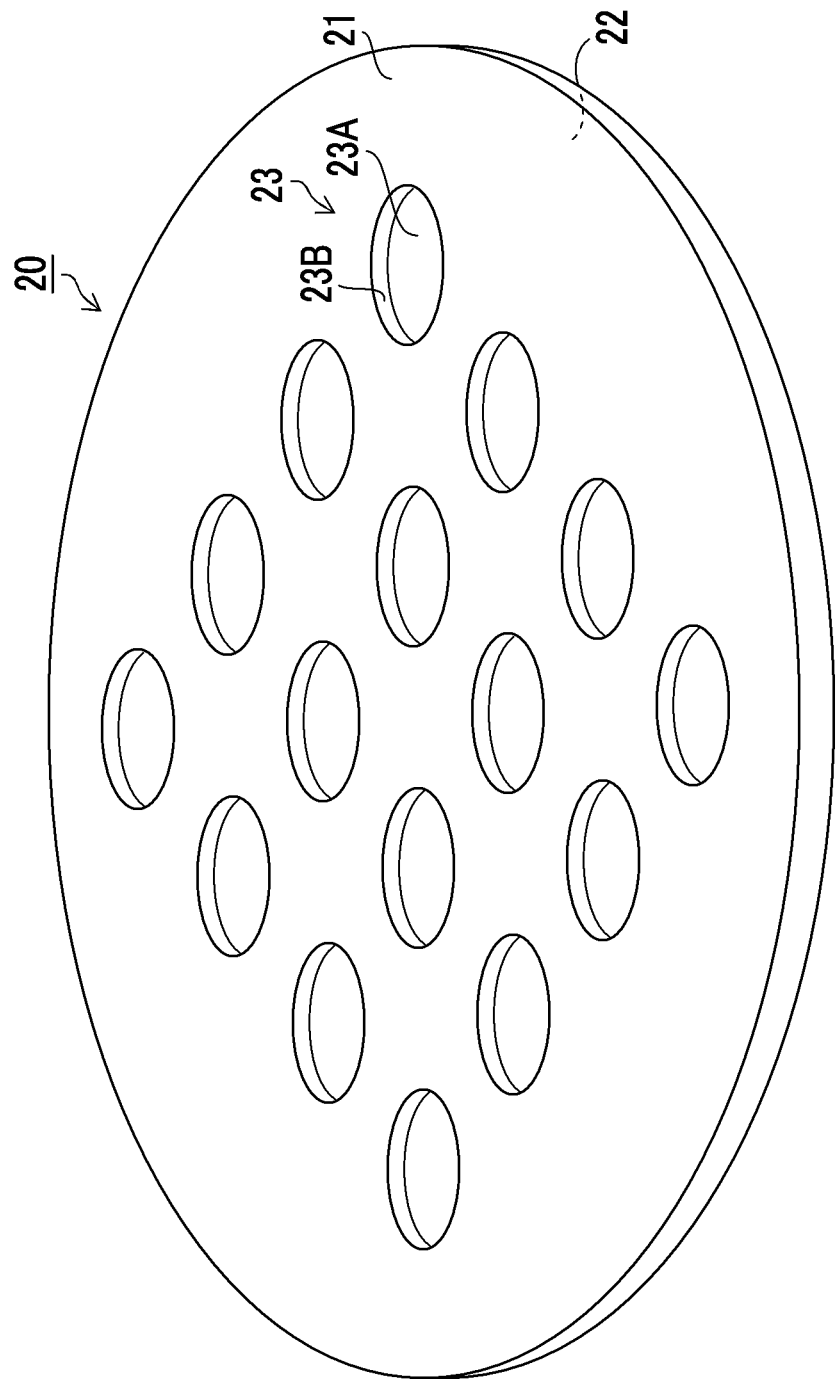
FIG. 2 is a perspective view of a thermoplastic resin plate.

In the resin plate preparation step, the thermoplastic resin plate is prepared. As illustrated in FIG. 2, a thermoplastic resin plate 20 has a main surface (flat surface) 21 and a main surface 22 which oppose each other, and is configured in a plate shape having a certain thickness. For example, the thermoplastic resin plate 20 can have a cylindrical shape having a thickness of 1 mm to 6 mm and a diameter of 150 mm to 300 mm. The shape of the thermoplastic resin plate 20 is not limited to the cylindrical shape, and may be a rectangular shape in a plan view.

A plurality of recessed step portions 23 are formed on the main surface 21 of the thermoplastic resin plate 20. The recessed step portion 23 is formed by a bottom surface 23A and a wall surface 23B surrounding the bottom surface 23A. The recessed step portion 23 has a volume equal to or less than the total volume of the protruding pattern 14 and the pedestal 11. However, in a case where the area of the bottom surface 23A of the recessed step portion 23 is caused to be the same as the area of the main surface 12 of the pedestal 11 or smaller than the area of the main surface 12 in a plan view, the height of the wall surface 23B of the recessed step portion 23 (hereinafter, also referred to as "the height of the recessed step portion 23"), that is, the length from the bottom surface 23A to the main surface 21 is caused to be shorter than the length from the main surface 12 of the pedestal 11 to the substrate 15 (hereinafter, referred to as "the height of the pedestal 11"). In the recessed pattern forming step, which will be described later, the height of the recessed step portion 23 is caused to be shorter than the height of the pedestal 11 by the height by which the amount of the resin that is pressed and pushed away in a case where the protruding pattern 14 and the pedestal 11 of the plate precursor 10 are pressed against the bottom surface 23A of the recessed step portion 23 flows out of the recessed step portion 23 and spreads by coming into contact with the main surface 21 and the substrate 15 of the plate precursor 10. Accordingly, the protruding pattern 14 formed on the main surface of the pedestal 11 can be pressed against the bottom surface 23A of the recessed step portion 23. For example, the length from the bottom surface 23A to the main surface 21 can be set to a length obtained by subtracting the height (50 µm) of the resin portion that is pushed away from the height (0.2 mm to 2 mm) of the pedestal 11.

The shape of the bottom surface 23A of the recessed step portion 23 is preferably the same shape as the main surface 12 of the pedestal 11 in a plan view. By causing the shape of the recessed step portion 23 to be the same as that of the main surface 12 and causing the area of the recessed step portion 23 to be the same as or smaller than the area of the main surface 12, the entire region of the recessed step portion 23 can be pressed by the main surface 12 of the pedestal 11. In addition, in a case where the length from the bottom surface 23A to the main surface 21 is caused to be the same as the length from the main surface 12 of the pedestal 11 to the substrate 15, the area of the recessed step portion 23 is increased by the amount of the resin pushed away by the protruding pattern 14, whereby the main surface 21 of a thermoplastic resin plate precursor to be manufactured can be made flat.

The thermoplastic resin forming the thermoplastic resin plate 20 is not particularly limited. For example, polyethylene terephthalate, polycarbonate, polymethyl methacrylate, polystyrene, linear low density polyethylene (LLDPE), liquid crystal polymers, polylactic acid, and the like can be suitably used. For example, the thermoplastic resin plate 20 can be manufactured by injection molding using a thermoplastic resin.

Figure 3:
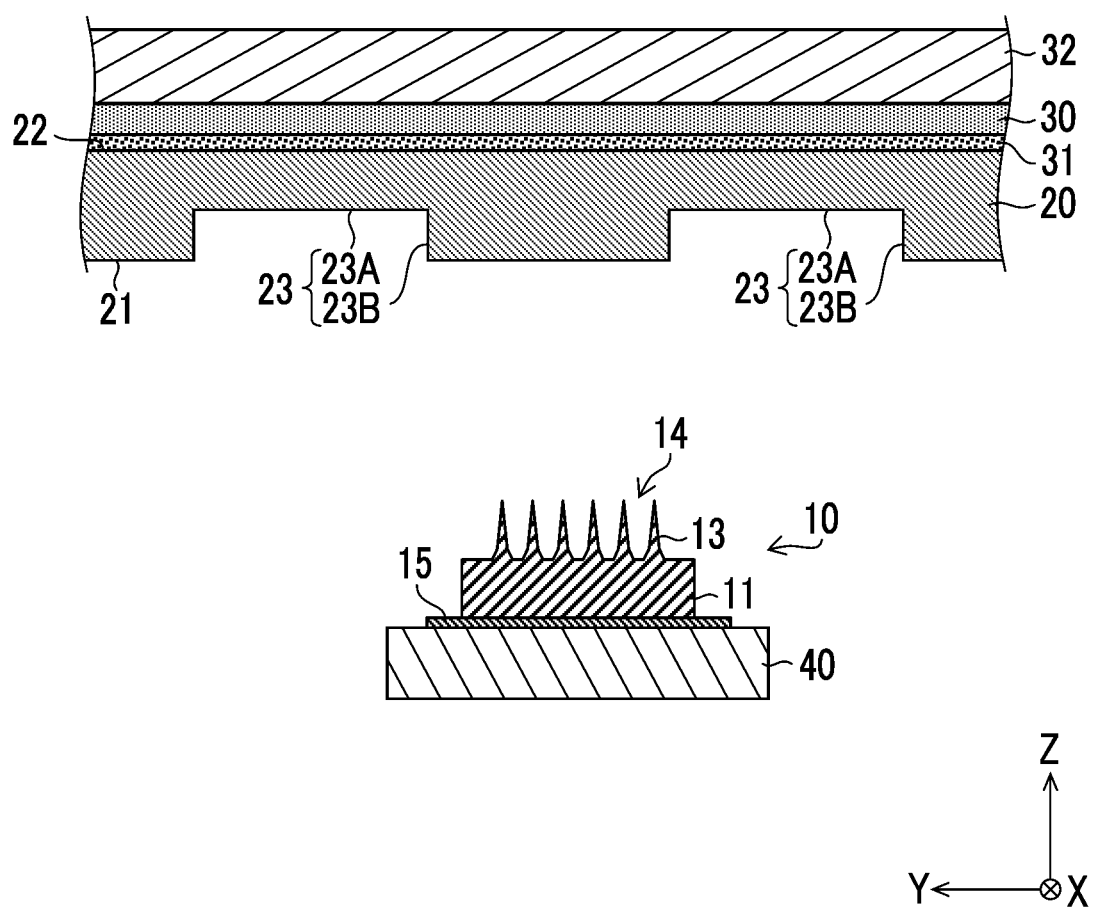
FIG. 3 is a step diagram illustrating a production method of a thermoplastic resin plate precursor.

As illustrated in FIG. 3, the thermoplastic resin plate 20 and a quartz substrate 30 are bonded by a double-sided adhesive film 31 on the main surface 22 side. The surface of the quartz substrate 30 on the side opposite to the double-sided adhesive film 31 is attached to a work stage 32. The work stage 32 has an X-axis drive mechanism and a Y-axis drive mechanism (not illustrated) that move in directions orthogonal to each other on a horizontal plane, and can move in an X direction and a Y direction.

For example, the quartz substrate 30 preferably has the same shape and the same area as the thermoplastic resin plate 20 in a plan view. The quartz substrate 30 functions as a reinforcing member for maintaining the rigidity of the thermoplastic resin plate 20.

The plate precursor 10 having the protruding pattern 14 is attached to a plate precursor stage 40. The plate precursor stage 40 has a Z-axis drive mechanism (not illustrated) and can move along a Z-axis direction. The plate precursor 10 is heated to a temperature at which the thermoplastic resin plate 20 is softened. Heating is performed by a heater (not illustrated). Depending on the thermoplastic resin forming the thermoplastic resin plate 20, the plate precursor 10 is heated to an appropriate temperature.

The protruding pattern 14 of the plate precursor 10 and the bottom surface 23A of the thermoplastic resin plate 20 are arranged so as to face each other.

Next, the resin plate precursor production step will be described. The resin plate precursor production step includes the positioning step and the recessed pattern forming step.

Figure 4:
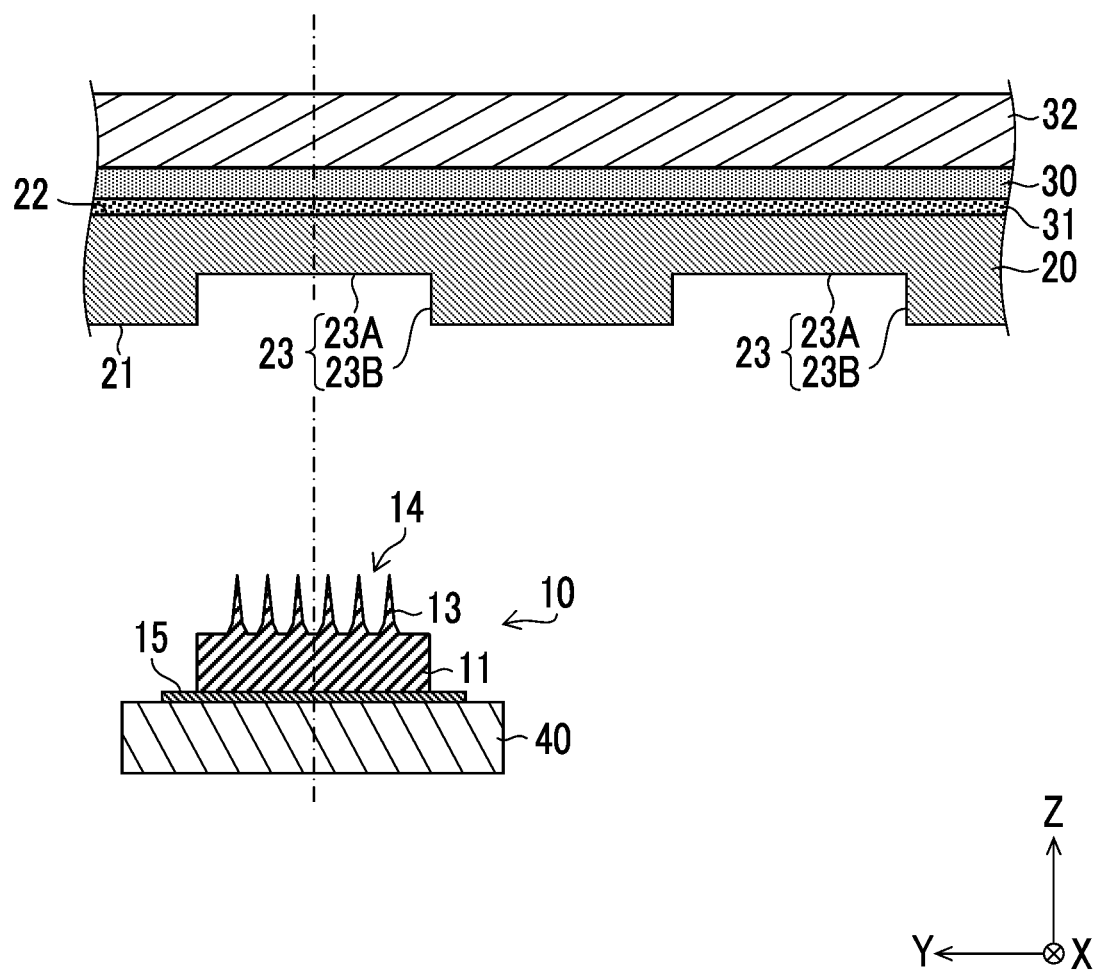
FIG. 4 is a step diagram illustrating the production method of a thermoplastic resin plate precursor.

In the positioning step illustrated in FIG. 4, the plate precursor 10 and the thermoplastic resin plate 20 are moved relative to each other such that the plate precursor 10 and the center position of the recessed step portion 23 are positioned. In the positioning step of the embodiment, the work stage 32 that supports the thermoplastic resin plate 20 is moved by driving the X-axis drive mechanism and the Y-axis drive mechanism (not illustrated) such that the center position of the recessed step portion 23 and the plate precursor 10 are positioned. In the positioning, the center position of the recessed step portion 23 and the center position of the protruding pattern 14 are positioned.

As long as the plate precursor 10 and the thermoplastic resin plate 20 can be moved relative to each other, either one or both of the plate precursor 10 or the thermoplastic resin plate 20 may be moved.

Figure 25:
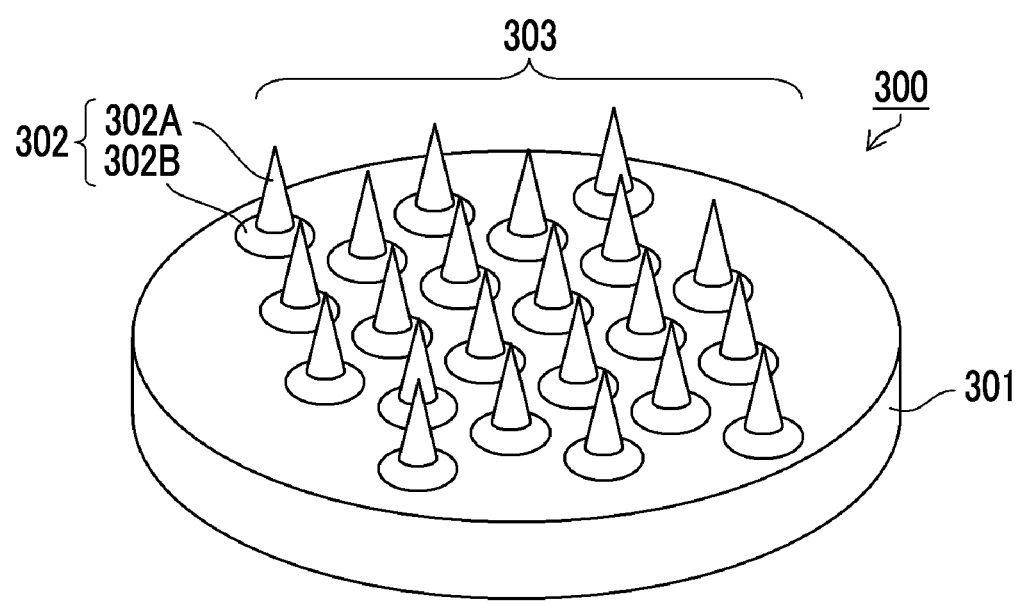
FIG. 25 is a perspective view of the pattern sheet.

Since the center position of the recessed step portion 23 and the plate precursor 10 are positioned, a protruding pattern 303 of a pattern sheet 300 and the center position of a sheet portion 301 illustrated in FIG. 25 can be positioned.

Figure 5:
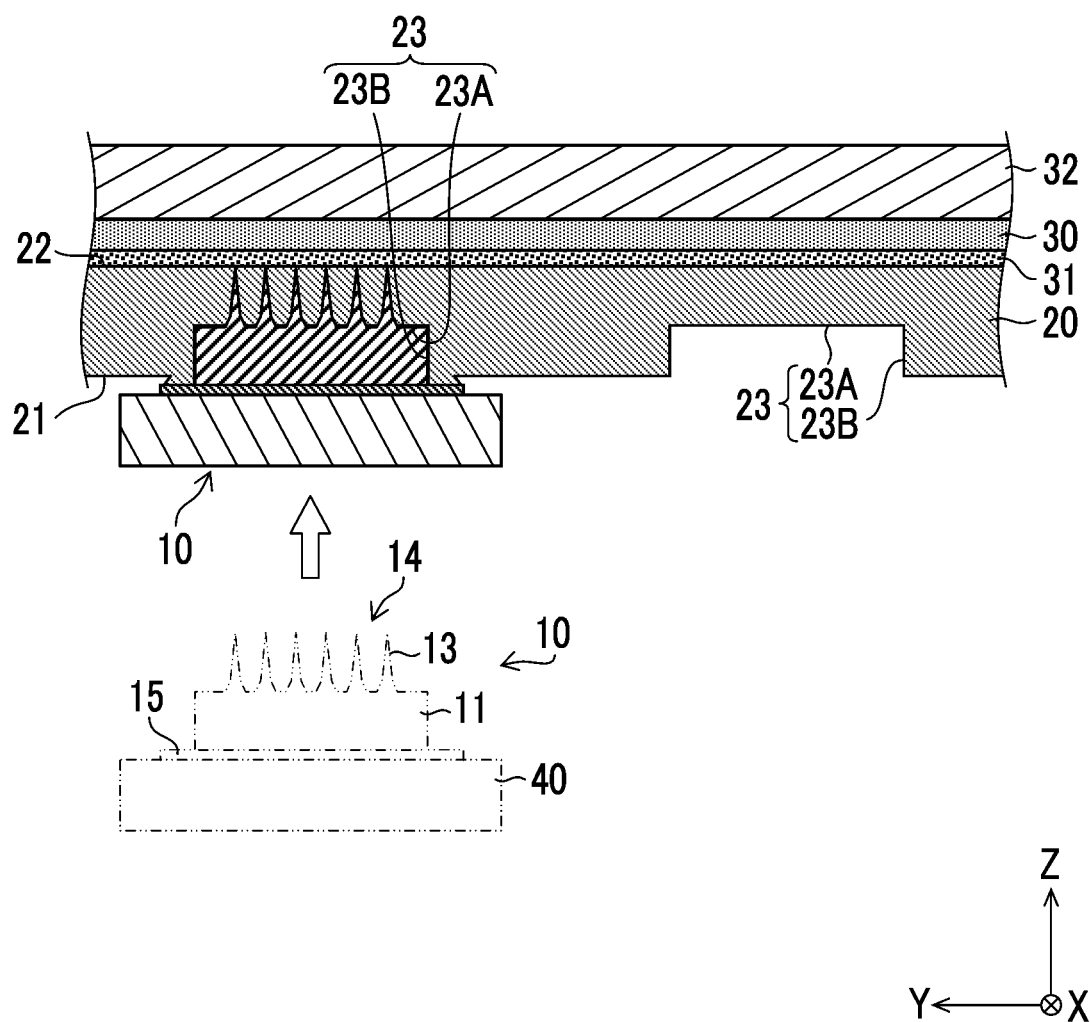
FIG. 5 is a step diagram illustrating the production method of a thermoplastic resin plate precursor.

Next, in the recessed pattern forming step illustrated in FIG. 5, the heated protruding pattern 14 of the plate precursor 10 is pressed against the bottom surface 23A of the thermoplastic resin plate 20. As illustrated in FIG. 5, the plurality of protruding portions 13 forming the protruding pattern 14 are pressed against the bottom surface 23A of the thermoplastic resin plate 20.

In the plate precursor 10 and the thermoplastic resin plate 20 illustrated in FIG. 5, the main surface 12 of the pedestal 11 and the recessed step portion 23 are the same in area and shape, and the height of the pedestal 11 is lower than the height of the recessed step portion 23 by the amount of the resin pushed away by the protruding pattern 14. In a case where the plate precursor 10 is pressed against the thermoplastic resin plate 20, the pedestal 11 of the plate precursor 10 presses the bottom surface 23A and the wall surface 23B of the recessed step portion 23 such that the recessed step portion 23 is transferred to the inverted shape of the pedestal 11 and the protruding pattern 14. The resin corresponding to recesses 24 (see FIG. 6) formed by pressing the plate precursor 10 flows into the gap between the substrate 15 of the plate precursor 10 and the main surface 21 of the thermoplastic resin plate 20 as illustrated in FIG. 5. The resin that has flowed in spreads between the substrate 15 and the main surface 21.

In the pressing of the embodiment, by driving the Z-axis drive mechanism, the plate precursor 10 is moved along the Z direction toward the bottom surface 23A such that the protruding pattern 14 is pressed against the bottom surface 23A. As long as the protruding pattern 14 can be pressed against the bottom surface 23A, either one or both of the plate precursor 10 and the thermoplastic resin plate 20 may be moved in the Z direction.

The protruding pattern 14 of the heated plate precursor 10 is pressed against the bottom surface 23A of the recessed step portion 23 with a predetermined pressing force and a time. The bottom surface 23A of the thermoplastic resin plate 20 is heated to the softening temperature or higher by pressing the protruding pattern 14 of the heated plate precursor 10. By cooling the plate precursor 10 in a state where the pressed protruding pattern 14 is in contact with the bottom surface 23A of the thermoplastic resin plate 20, the thermoplastic resin plate 20 is cooled to a softening temperature or lower.

As described above, the height of the pedestal 11 is set in consideration of the height of the recessed step portion 23 and the resin that is pushed away by the pressing. In a case where the height of the pedestal 11 is increased and the substrate 15 and the resin that is pushed away do not come into contact with each other, the shape of the surface of the produced thermoplastic resin plate precursor is not stable, which is not preferable. Furthermore, in a case where the main surface 12 of the pedestal 11 and the bottom surface 23A of the recessed step portion 23 do not come into contact with each other, the protruding portions 13 of the protruding pattern 14 are not stably transferred to the recessed step portion 23, which is not preferable. In a case where the resin that is pushed away corresponds to the volume of the protruding pattern 14, for example, by causing the height of the pedestal 11 to be higher than the height of the recessed step portion by 50 µm, a recessed step portion having a well-shaped recessed pattern can be formed.

Figure 6:
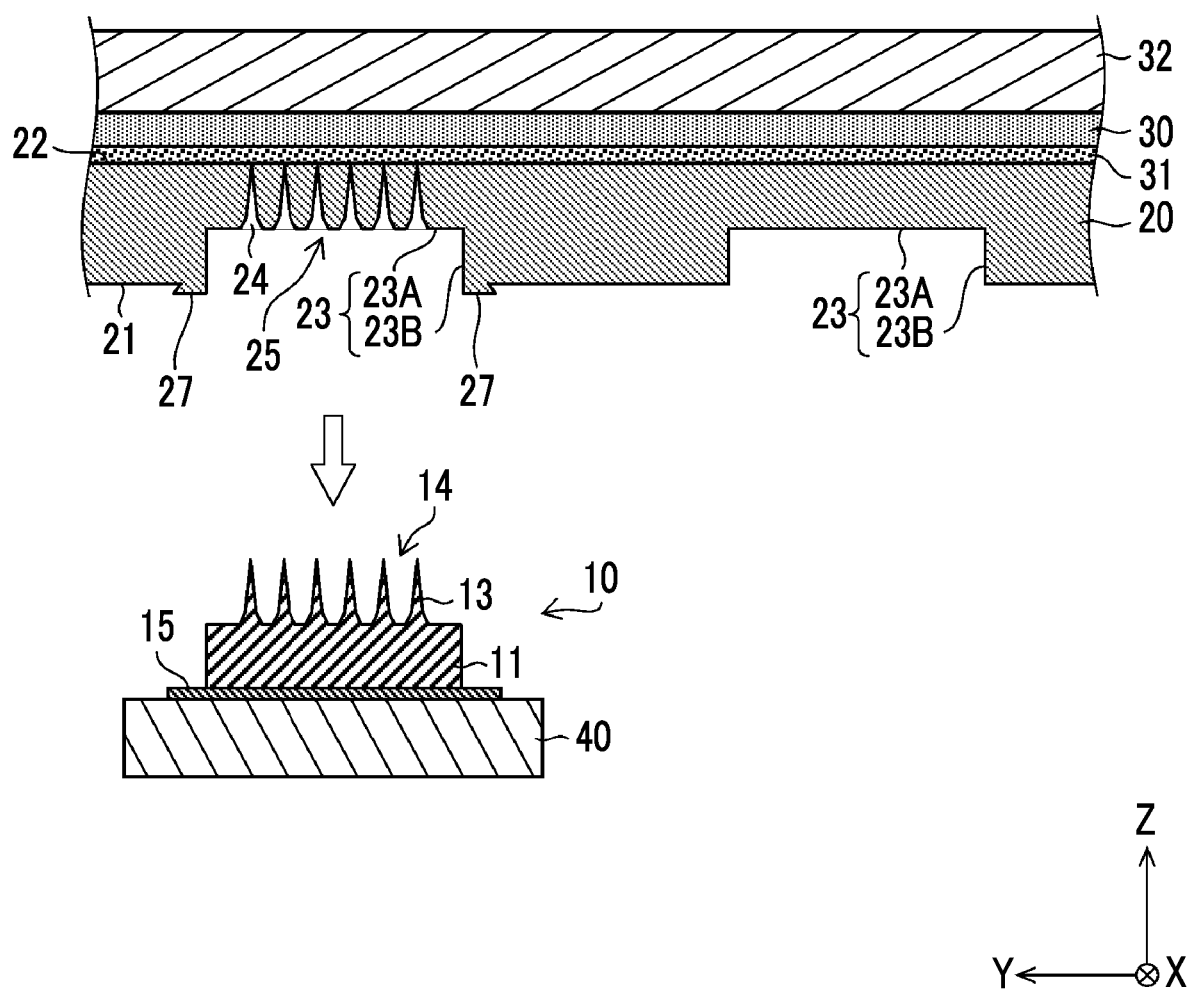
FIG. 6 is a step diagram illustrating the production method of a thermoplastic resin plate precursor.

Next, in the recessed pattern forming step illustrated in FIG. 6, the plate precursor 10 and the thermoplastic resin plate 20 are separated from each other. On the bottom surface 23A of the thermoplastic resin plate 20, a plurality of the recesses 24 that are the inverted shapes of the plurality of protruding portions 13 are formed. By arranging the plurality of recesses 24 on the bottom surface 23A of the thermoplastic resin plate 20, a recessed pattern 25 is formed. Furthermore, the main surface 21 of the thermoplastic resin plate 20 has a protrusion 27 formed continuously from the recessed step portion 23. The surface of the protrusion 27 spreads along the substrate 15 of the plate precursor 10 and is thus formed flat. Among the side surfaces of the protrusion 27, the side surface on the recessed step portion 23 side is pressed by the pedestal 11 of the plate precursor 10, and is thus formed continuously from the wall surface 23B of the recessed step portion 23. Furthermore, regarding the side surface on the opposite side, since the resin pushed away spreads along the substrate 15 of the plate precursor 10 in the case where the plate precursor is pressed, the surface side of the protrusion 27 spreads toward the main surface 21 side of the thermoplastic resin plate 20. Therefore, the protrusion 27 is configured in an inverted tapered structure which spreads from the main surface 21 of the thermoplastic resin plate 20 toward the surface of the protrusion 27. In the pressing of the embodiment, by driving the Z-axis drive mechanism, the plate precursor 10 is moved in the direction away from the bottom surface 23A along the Z direction, such that the plate precursor 10 and the thermoplastic resin plate 20 are separated from each other.

Figure 7:
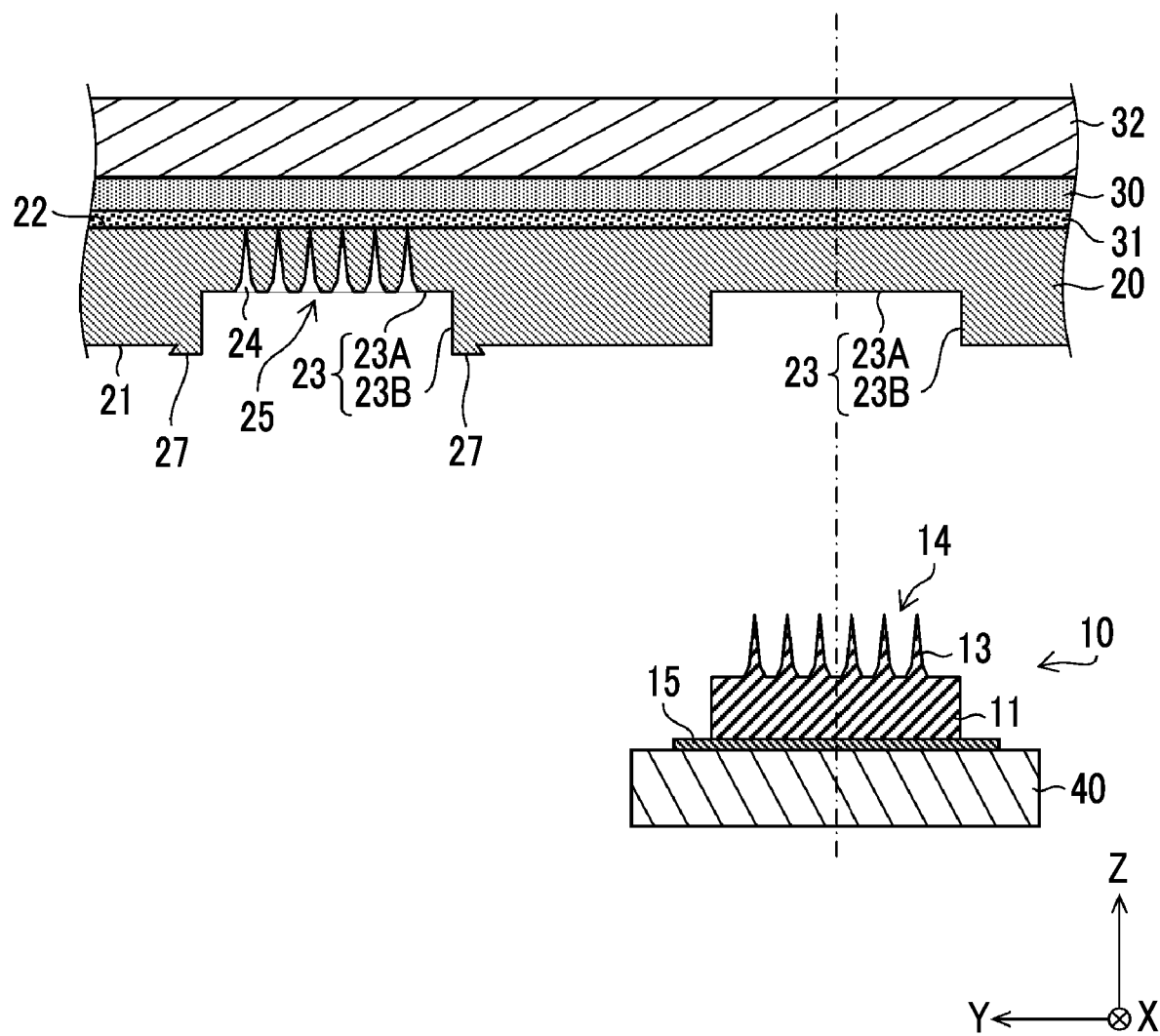
FIG. 7 is a step diagram illustrating the production method of a thermoplastic resin plate precursor.

In a case where the recessed pattern 25 is formed in the recessed step portion 23, the plate precursor 10 and the thermoplastic resin plate 20 are moved relative to each other in the positioning step illustrated in FIG. 7, such that the plate precursor 10 and the center position of the recessed step portion 23 where the recessed pattern 25 is not formed are positioned. As in FIG. 4, the center position of the recessed step portion 23 and the plate precursor 10 are positioned by moving the work stage 32 that supports the thermoplastic resin plate 20.

Figure 8:
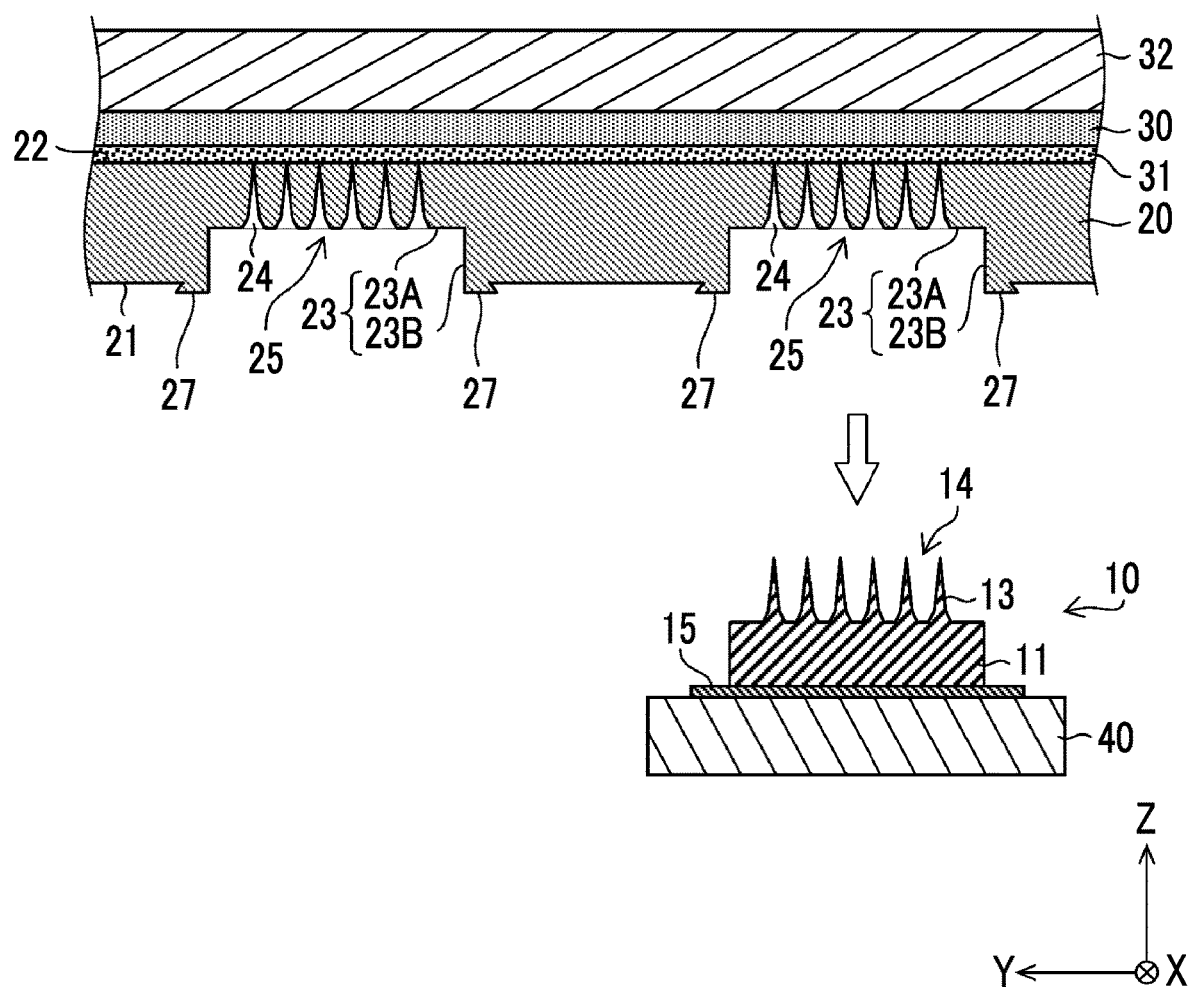
FIG. 8 is a step diagram illustrating the production method of a thermoplastic resin plate precursor.

In the recessed pattern forming step illustrated in FIG. 8, similarly to FIGS. 5 and 6, the protruding pattern 14 of the heated plate precursor 10 is pressed against the bottom surface 23A of the thermoplastic resin plate 20. The protruding pattern 14 of the heated plate precursor 10 is pressed against the bottom surface 23A of the recessed step portion 23 with a predetermined pressing force and a time. Next, the plate precursor 10 is cooled in a state where the pressed protruding pattern 14 is in contact with the bottom surface 23A of the thermoplastic resin plate 20. By separating the plate precursor 10 and the thermoplastic resin plate 20 from each other, a plurality of the recesses 24 that are the inverted shapes of the plurality of protruding portions 13 are formed on the bottom surface 23A of the thermoplastic resin plate 20. Until the recessed pattern 25 is formed in all the recessed step portions 23 of the thermoplastic resin plate 20, the positioning step and the recessed pattern forming step illustrated in FIGS. 4 to 8 are repeated. By forming the recessed pattern 25 in all the recessed step portions 23 of the thermoplastic resin plate 20, a thermoplastic resin plate precursor 26 is produced from the thermoplastic resin plate 20.

Next, in the positioning step, a method for calculating the positional deviation amount of the plate precursor 10 and a method for calculating the center position of the recessed step portion 23 of the thermoplastic resin plate 20 will be described.

As illustrated in FIG. 3, the plate precursor 10 is attached to the plate precursor stage 40 having the Z-axis drive mechanism (not illustrated). The laminate in which the thermoplastic resin plate 20 and the quartz substrate 30 are laminated is attached to the work stage 32 having the X-axis drive mechanism and the Y-axis drive mechanism (not illustrated) which are installed to face the plate precursor 10. The X axis, Y axis, and Z axis in this state are defined as $X_0$, $Y_0$, and $Z_0$.

Figure 9:
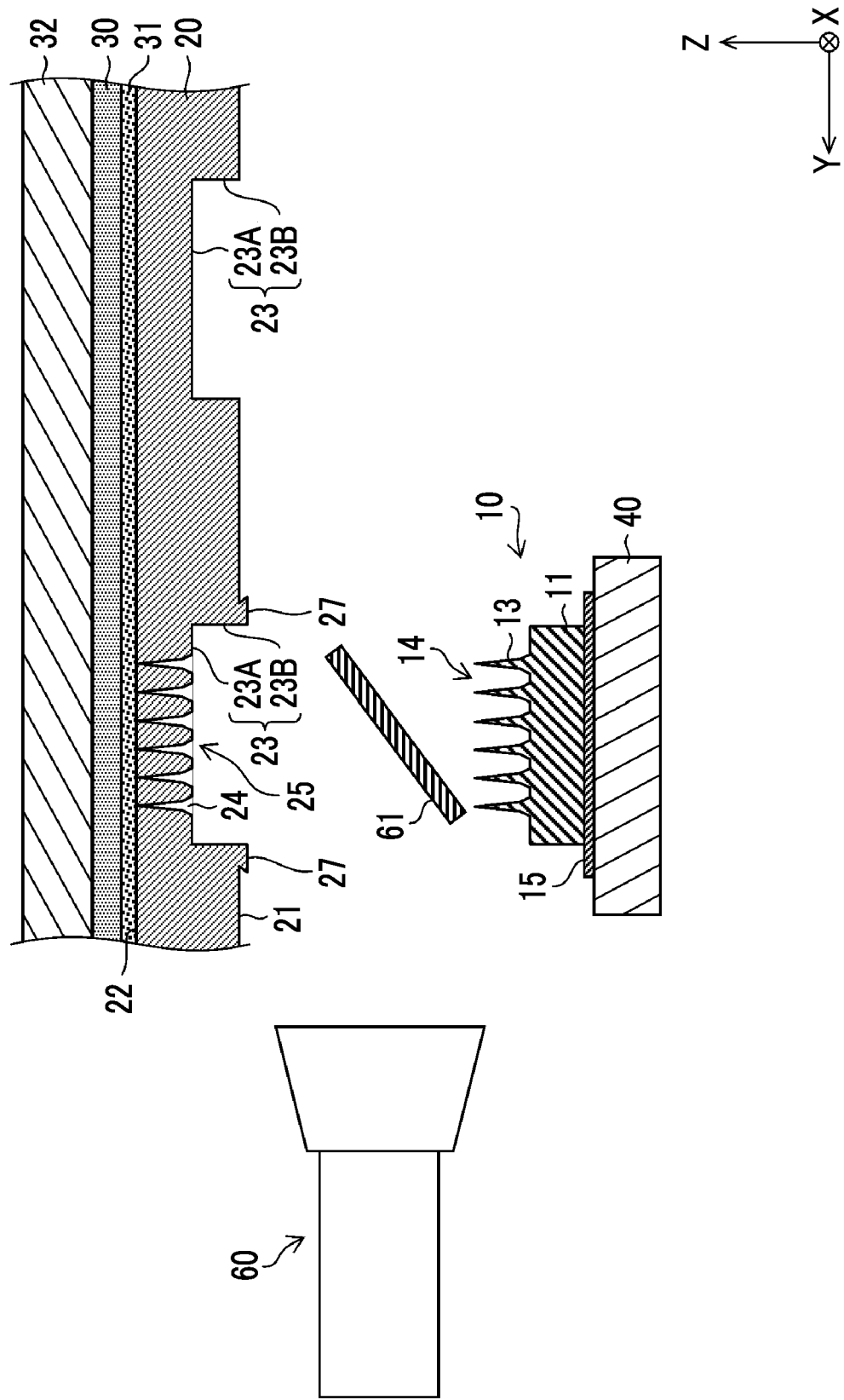
FIG. 9 is a step diagram illustrating the production method of a thermoplastic resin plate precursor.

A method of calculating a positional deviation amount of the plate precursor 10 will be described with reference to FIG. 9. The work stage 32 is moved to predetermined coordinates $(X_{ib}, Y_{ib})$. The heated plate precursor 10 is pressed against the bottom surface 23A of the recessed step portion 23 of the thermoplastic resin plate 20 in the Z-axis direction by the plate precursor stage 40. Next, the plate precursor 10 is separated from the thermoplastic resin plate 20 after being cooled, and the plate precursor 10 is returned to the initial position $Z_0$ by the plate precursor stage 40. The inverted structure of the protruding pattern 14 is transferred to the bottom surface 23A $(X_{ib}, Y_{ib})$ of the thermoplastic resin plate 20, such that the recessed pattern 25 is formed.

An imaging device 60 included in an image processing system is disposed at a position of a fixed point $(X_c, Y_c, Z_c)$. As illustrated in FIG. 9, the imaging device 60 is installed at a position where the optical axis of the imaging device 60 is parallel to an installation surface of the work stage 32, that is, the surface on which the quartz substrate 30 is installed. A mirror 61 is installed on the optical axis of the imaging device 60 and between the thermoplastic resin plate 20 and the plate precursor 10. A light source is irradiated in the same direction as the optical axis of the imaging device 60. The imaging device 60 comprises an imaging element such as a charge coupled device (CCD) or a complementary metal oxide semiconductor (CMOS).

A center $(X_{im}, Y_{im})$ of the recessed pattern 25 formed at the position $(X_{ib}, Y_{ib})$ of the thermoplastic resin plate 20 is detected by the imaging device 60 installed at the fixed point. As the positional deviation amount of the plate precursor 10, $(X_{ib} - X_{im})$ for the X direction and $(Y_{ib} - Y_{im})$ for the Y direction can be calculated.

Figure 10:
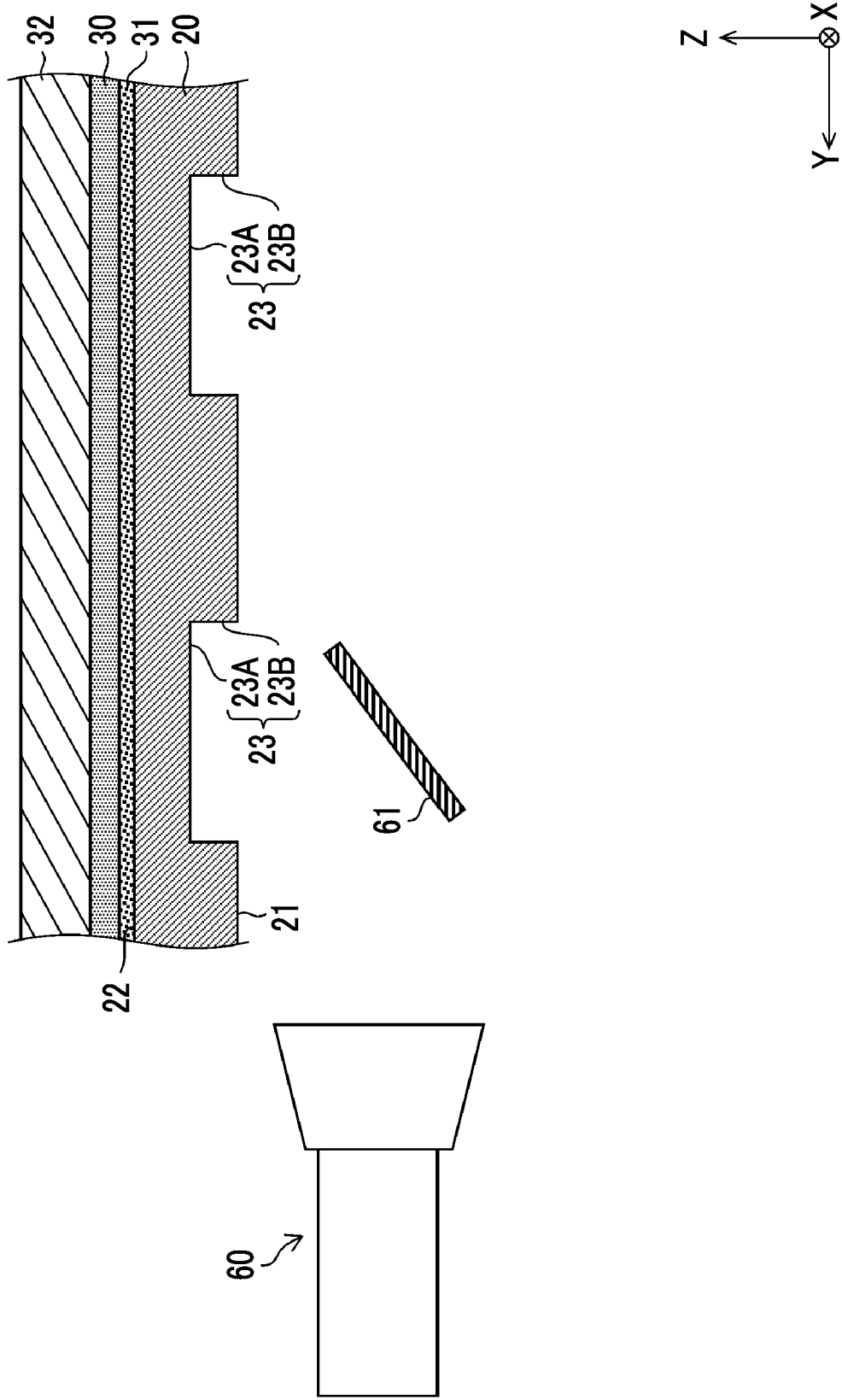
FIG. 10 is a step diagram illustrating the production method of a thermoplastic resin plate precursor.

A method of calculating the center position of the recessed step portion 23 of the thermoplastic resin plate 20 will be described with reference to FIG. 10. In a state where the imaging device 60 is fixed to the fixed point $(X_c, Y_c, Z_c)$, the thermoplastic resin plate 20 is moved in the X direction and the Y direction by the work stage 32 to detect the coordinates $(X_n, Y_n)$ of the center position of all k recessed step portions 23 formed in the thermoplastic resin plate 20 (here, n=1 to k).

In the positioning step, the work stage 32 is moved to $(X_1-(X_{ib}-X_{im}), Y_1-(Y_{ib}-Y_{im}))$ based on the calculated center position of the recessed step portion 23 and the result of the positional deviation amount of the plate precursor 10. The center position of the recessed step portion 23 at n=1 can be caused to coincide with the center position of the protruding pattern 14 of the plate precursor 10. The term "coincide" includes a case of perfect coincidence and a case of having an allowable deviation. The heated plate precursor 10 is moved along the Z direction by the plate precursor stage 40. The protruding pattern 14 is pressed against the bottom surface 23A of the recessed step portion 23 with a constant pressing force and a time. After the plate precursor 10 is cooled, the plate precursor 10 is separated from the thermoplastic resin plate 20 and returned to the $Z_0$ position. The recessed pattern 25 can be formed at the center position $(X_1, Y_1)$ of the recessed step portion 23 at n=1 formed in the thermoplastic resin plate 20. For the remaining (k−1) recessed step portions 23 (n=2 to k), the work stage 32 is moved to $(X_n-(X_{ib}-X_{im}), Y_n-(Y_{ib}-Y_{im}))$. In the same manner as described above, the heated plate precursor 10 is pressed by the plate precursor stage 40. After the plate precursor 10 is cooled, the plate precursor 10 is separated from the thermoplastic resin plate 20 and returned to the $Z_0$ position. By repeating the positioning step and the recessed pattern forming step, the recessed pattern 25 that is the inverted structure of the protruding pattern 14 can be formed at the center position $(X_n, Y_n)$ of the k recessed step portions 23 (here, n=1 to k). In a case where the series of steps are finished, the thermoplastic resin plate precursor 26 in which the recessed pattern 25 is formed in the plurality of recessed step portions 23 is produced. In the thermoplastic resin plate precursor 26 of the embodiment, in FIG. 8, the center position of the recessed pattern 25 and the center position of the recessed step portion 23 coincide with each other.

Figure 11:
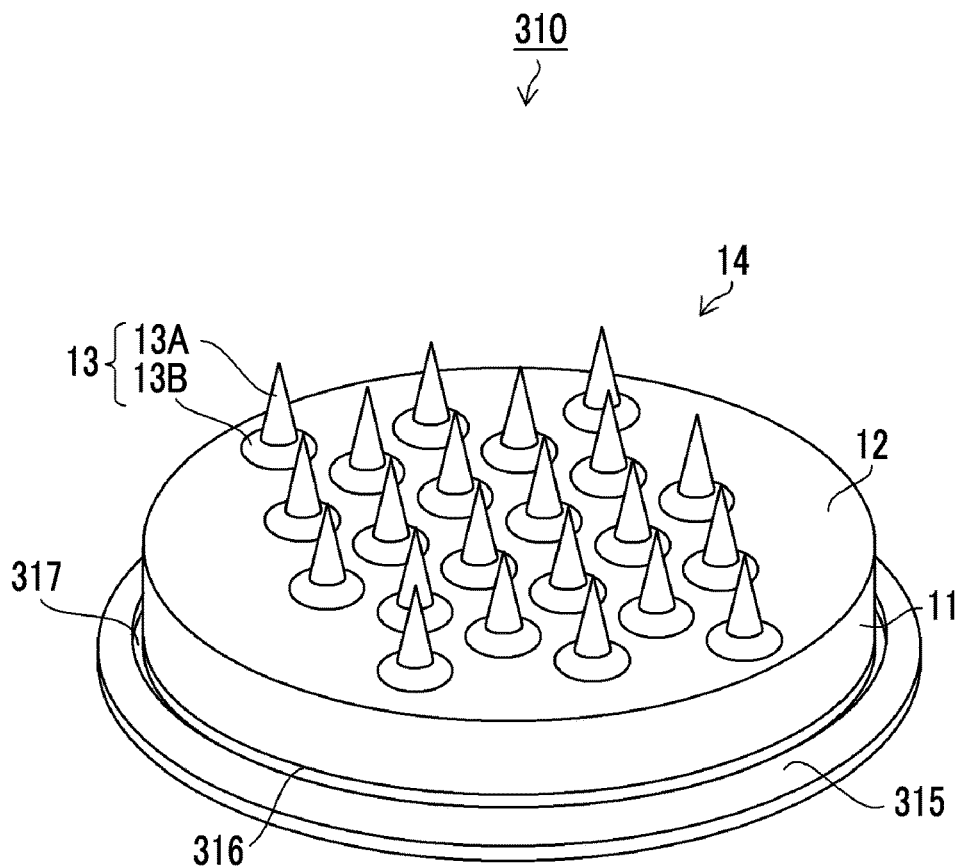
FIG. 11 is a perspective view illustrating another example of the plate precursor.

FIG. 11 is a perspective view illustrating another example of the plate precursor. A plate precursor 310 illustrated in FIG. 11 is different from the plate precursor 10 illustrated in FIG. 1 in that a substrate 315 has a through-hole 317. The through-hole 317 is formed through the substrate 315 in the height direction of the pedestal 11 along the side surface of the pedestal 11 at an edge portion 316 where the side surface of the pedestal 11 and the substrate 315 are in contact with each other. By providing the through-hole 317, air in the recessed step portion 23 in a case of pressing the plate precursor 10 against the recessed step portion 23 can be released from the through-hole 317. By allowing the air to be released from the through-hole 317, it is possible to prevent the air from being collected at the contact portion between the plate precursor 10 and the thermoplastic resin plate 20. Therefore, the shape of the recessed step portion 23 after forming the recessed pattern can be stably formed. In the plate precursor 310 illustrated in FIG. 11, the through-hole 317 provided in the substrate 315 is formed over one circumference along the side surface of the pedestal 11. However, during use, since the plate precursor 310 is attached to the plate precursor stage 40 to be used, the substrate 315 can be used even in a case of being divided by the through-hole 317.

Figure 12:
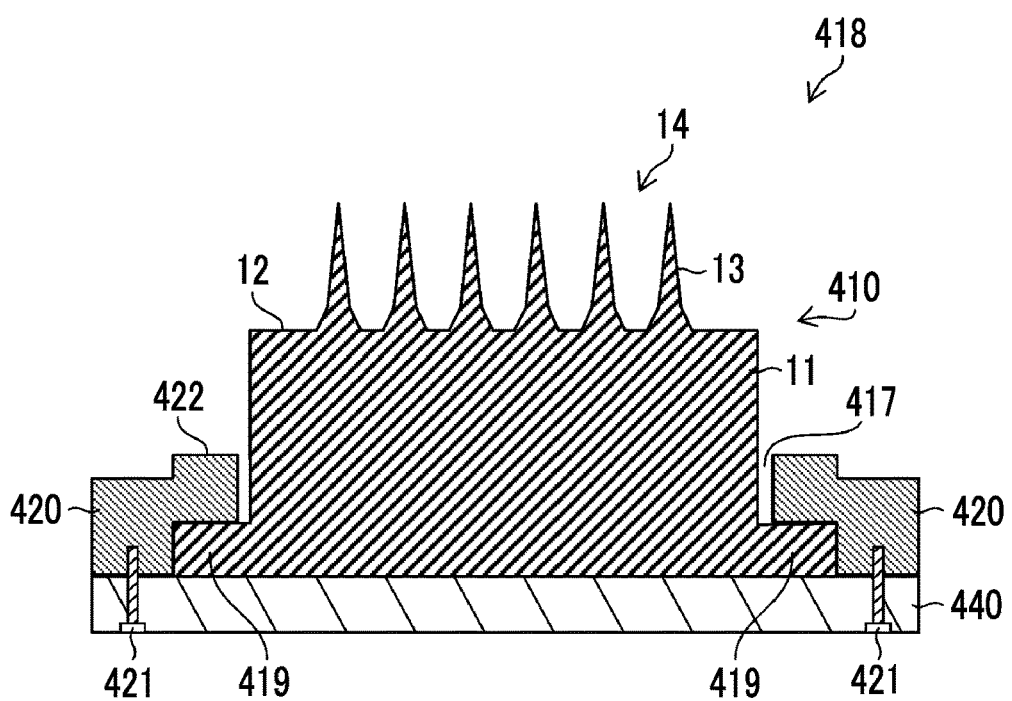
FIG. 12 is a cross-sectional view illustrating a structure having a through-hole in a state where a plate precursor is attached to a plate precursor stage.

FIG. 12 is a cross-sectional view illustrating a structure 418 having a through-hole 417 in a state where a plate precursor 410 is attached to a plate precursor stage 440. The plate precursor 410 illustrated in FIG. 12 has a protrusion 419 at the side surface of the pedestal 11 on an end portion on the side opposite to the main surface 12. The plate precursor 410 is attached to the plate precursor stage 440 by sandwiching the protrusion 419 between the plate precursor stage 440 and a holding member 420. The plate precursor stage 440 and the holding member 420 can be attached by screws 421. The through-hole 417 is formed by the side surface of the pedestal 11 and the side surface of the holding member 420. In the structure 418 in FIG. 12, a protruding surface 422 of the holding member 420 on the side opposite to the plate precursor stage 440 has the same function as the substrate 315 illustrated in FIG. 11.

Figure 13:
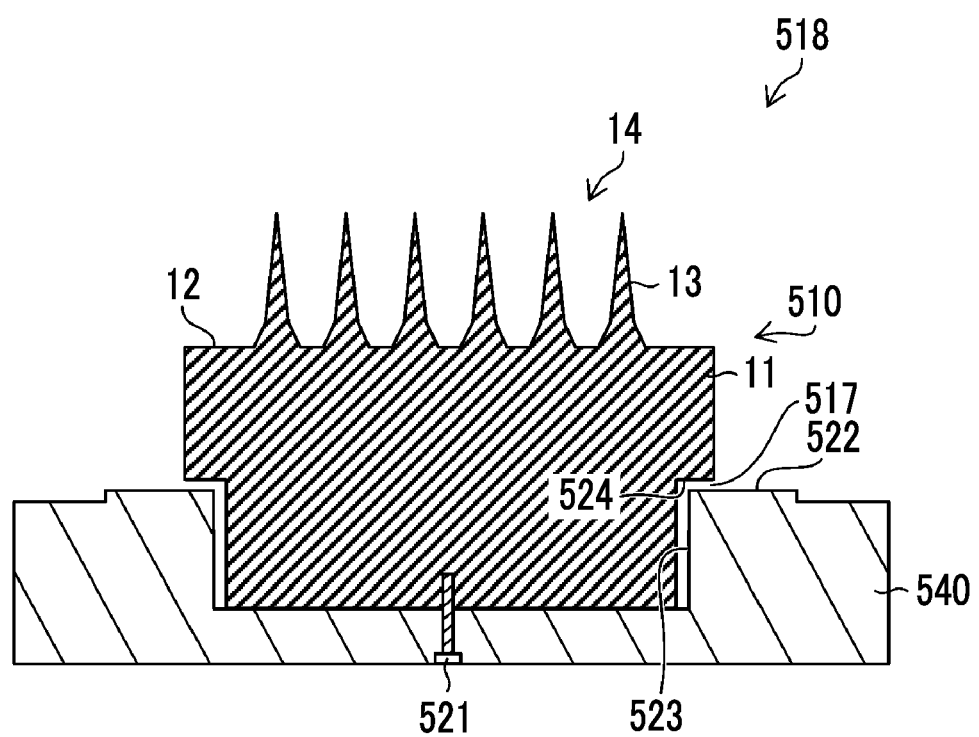
FIG. 13 is a cross-sectional view illustrating another structure having a through-hole in a state where a plate precursor is attached to a plate precursor stage.

FIG. 13 is a cross-sectional view illustrating a structure 518 having a through-hole 517 in a state where a plate precursor 510 is attached to a plate precursor stage 540. The plate precursor stage 540 of the structure 518 illustrated in FIG. 13 has a recess 523 in which a part of the plate precursor 510 is stored in the center. The side of the plate precursor 510 opposite to the main surface 12 is configured to have a diameter smaller than the diameter of the main surface 12 through a step portion 524 so as to be accommodated in the recess 523. The plate precursor stage 540 and the plate precursor 510 can be attached by a screw 521. A through-hole 517 is formed in a left-right direction in FIG. 13 by a protruding surface 522 provided in the plate precursor stage 540 and the step portion 524 of the plate precursor 510. In addition, the through-hole 517 is formed continuously in the height direction by forming a gap between the inner peripheral surface of the recess 523 and the side surface of the plate precursor 510. Also in the structure 518 illustrated in FIG. 13, the protruding surface 522 formed on the plate precursor stage 540 has the same function as the substrate 315 illustrated in FIG. 11.

Figure 14:
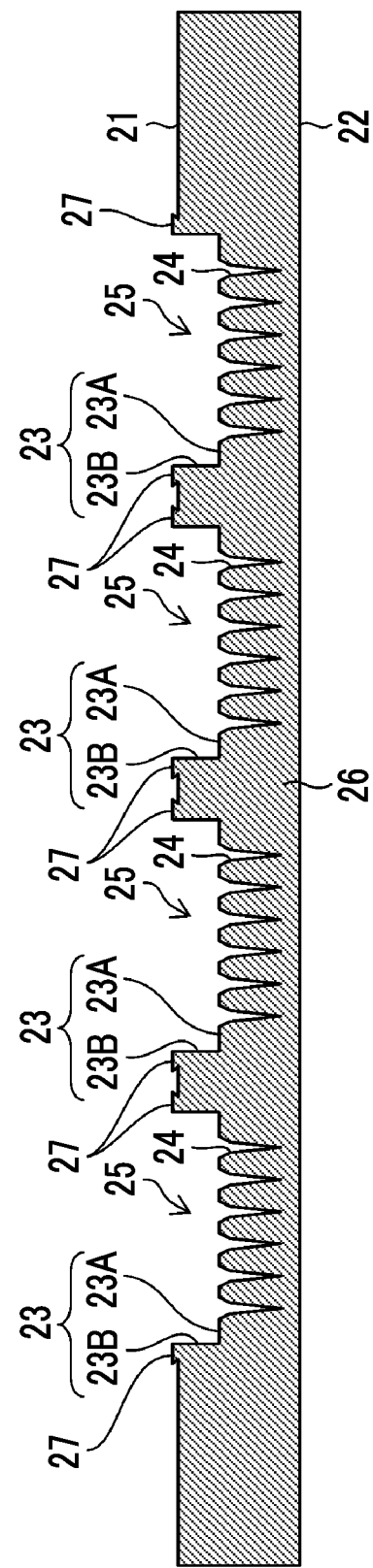
FIG. 14 is a step diagram illustrating a production method of a die by an electroforming treatment.

Next, a die production step of producing a die having a protruding step portion in which a protruding pattern is disposed by an electroforming treatment using the thermoplastic resin plate precursor 26 will be described. As illustrated in FIG. 14, the thermoplastic resin plate precursor 26 in which the recessed pattern 25 is formed in the plurality of recessed step portions 23 is prepared. A conduction treatment is performed on the thermoplastic resin plate precursor 26. In the conduction treatment, a metal film (for example, nickel) is formed on the main surface 21, the bottom surfaces 23A and the wall surfaces 23B forming the recessed step portions 23, the plurality of recesses 24 forming the recessed patterns 25, and the protrusions 27 of the thermoplastic resin plate precursor 26 by vapor deposition, sputtering, or the like.

Figure 15:
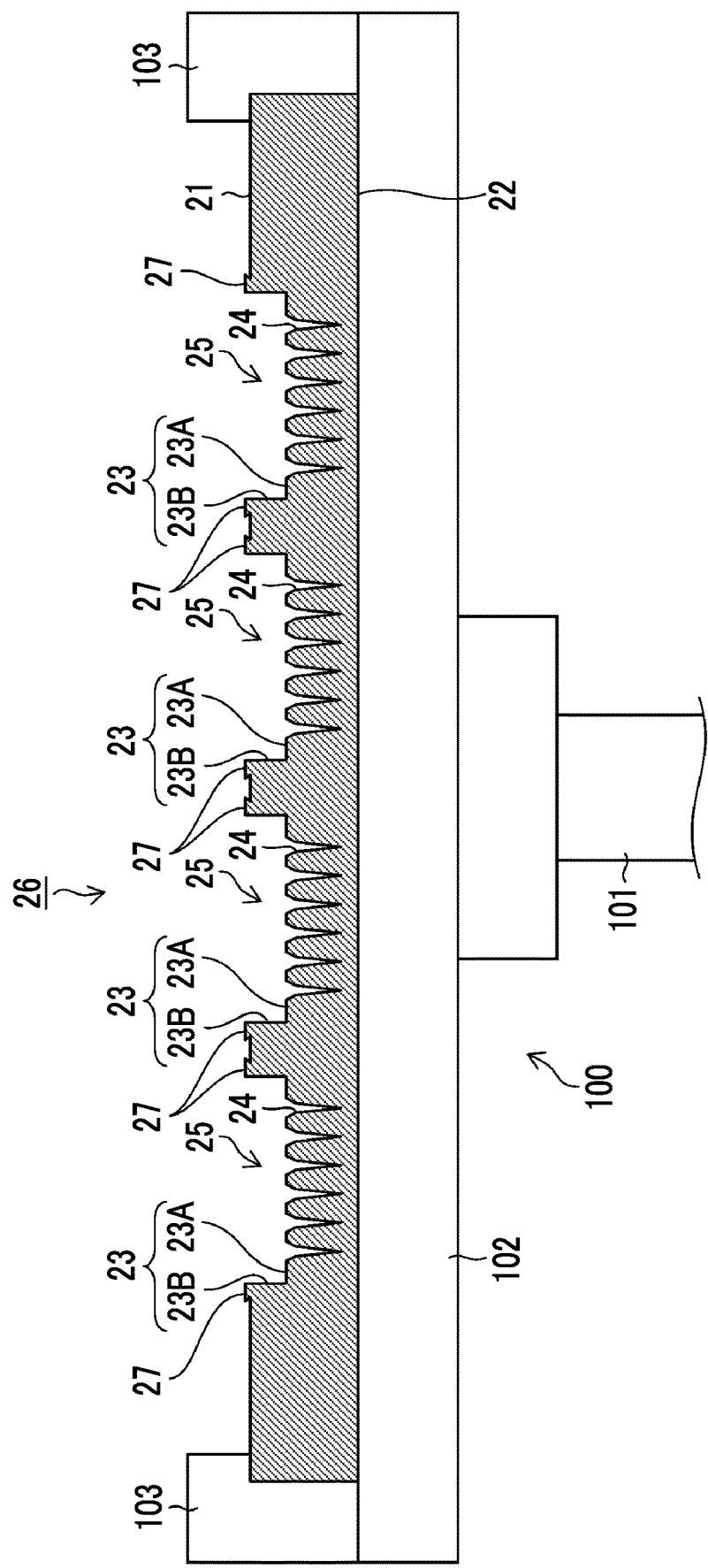
FIG. 15 is a step diagram illustrating the production method of a die by an electroforming treatment.

As illustrated in FIG. 15, the thermoplastic resin plate precursor 26 subjected to the conduction treatment is fixed to a cathode 100 used for the electroforming treatment. The cathode 100 comprises at least a shaft 101 or a cathode plate 102. The thermoplastic resin plate precursor 26 is fixed to the cathode plate 102 at a position where the main surface 22 of the thermoplastic resin plate precursor 26 and the cathode plate 102 face each other.

In order to supply a current from the cathode plate 102 to the metal film (not illustrated) formed on the thermoplastic resin plate precursor 26, a conductive ring 103 is provided at the outer peripheral portion of the thermoplastic resin plate precursor 26. The shaft 101 and the cathode plate 102 are formed of a conductive member. Here, the electroforming treatment refers to a treatment method of depositing metal on the thermoplastic resin plate precursor 26 by an electroplating method.

Figure 16:
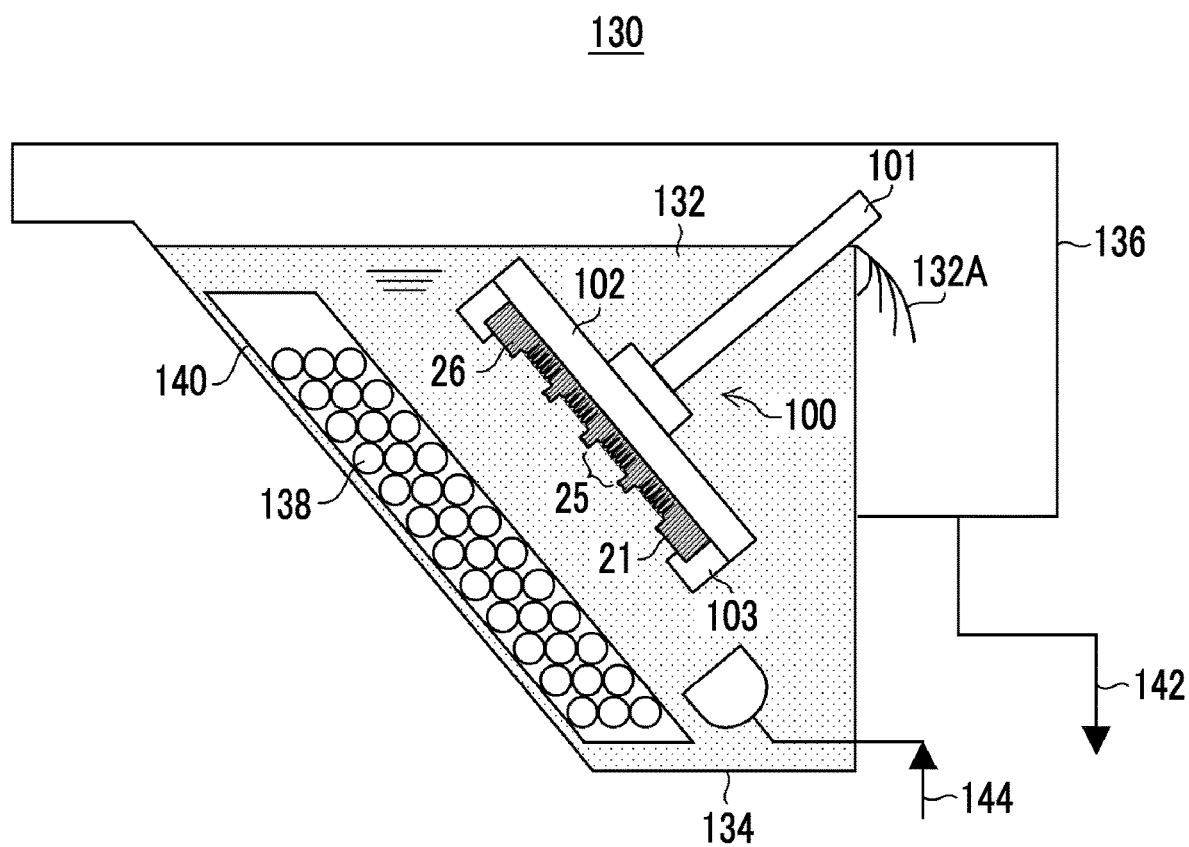
FIG. 16 is a step diagram illustrating the production method of a die by an electroforming treatment.

As illustrated in FIG. 16, the thermoplastic resin plate precursor 26 attached to the cathode 100 is immersed in an electroforming liquid 132. An electroforming apparatus 130 for performing the electroforming treatment on the thermoplastic resin plate precursor 26 comprises an electroforming tank 134 that holds the electroforming liquid 132, a drain tank 136 that receives an overflowing electroforming liquid 132A from the electroforming tank 134, and a titanium case 140 filled with Ni pellets 138. By immersing the cathode 100 having the thermoplastic resin plate precursor 26 attached thereto in the electroforming liquid 132, the electroforming apparatus 130 operates. As the electroforming liquid 132, for example, a liquid in which 400 g/L to 800 g/L of nickel sulfamate, 20 g/L to 50 g/L of boric acid, and necessary additives such as a surfactant (for example, sodium lauryl sulfate) are mixed can be used. The temperature of the electroforming liquid 132 is preferably 40° C. to 60° C.

A drain pipe 142 is connected to the drain tank 136, and a supply pipe 144 is connected to the electroforming tank 134. The electroforming liquid 132 overflowing from the electroforming tank 134 to the drain tank 136 is recovered by the drain pipe 142, and the recovered electroforming liquid 132 is supplied from the supply pipe 144 to the electroforming tank 134. The thermoplastic resin plate precursor 26 held by the cathode 100 is aligned with a position at which the main surface 21 on which the recessed patterns 25 are formed faces the titanium case 140 serving as an anode.

The cathode 100 is connected to a negative electrode, and a positive electrode is connected to the titanium case 140 serving as the anode. A direct current voltage is applied between the cathode 100 and the titanium case 140 while the thermoplastic resin plate precursor 26 held by the cathode plate 102 is rotated about the shaft 101 at a rotational speed of 10 rpm to 150 rpm. The Ni pellets 138 are dissolved, and a metal film is attached to the main surface 21, the bottom surfaces 23A and the wall surfaces 23B of the recessed step portions 23, and the inner walls of the recessed patterns 25 of the thermoplastic resin plate precursor 26 attached to the cathode 100.

Figure 17:
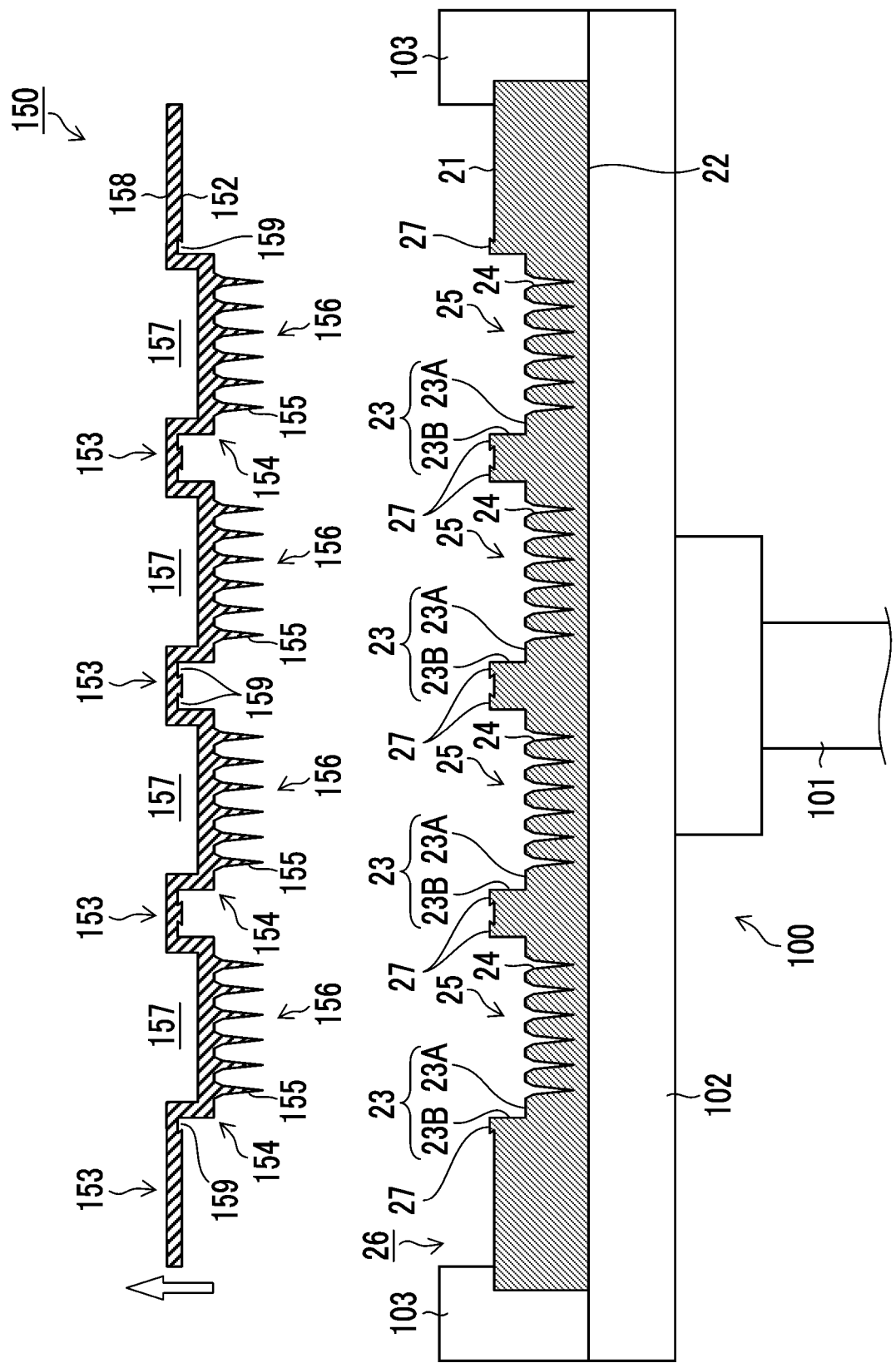
FIG. 17 is a step diagram illustrating the production method of a die by an electroforming treatment.

As an electroformed die 150 made of the metal film is formed on the thermoplastic resin plate precursor 26, as illustrated in FIG. 17, the cathode 100 to which the thermoplastic resin plate precursor 26 is attached is taken out from the electroforming tank 134 (not illustrated). Next, the die 150 is peeled from the thermoplastic resin plate precursor 26. The die 150 has a main surface 152 and a main surface 158 that oppose each other. The die 150 has flat portions 153 and protruding step portions 154 in a cross-sectional view. A plurality of protruding portions 155 are formed on the main surface 152 of the protruding step portion 154, and the plurality of protruding portions 155 form a protruding pattern 156. The protruding pattern 156 has an inverted shape of the recessed pattern 25 of the thermoplastic resin plate precursor 26. The protruding step portion 154 has an inverted shape of the recessed step portion 23. Furthermore, recesses 159 corresponding to the protrusions 27 of the thermoplastic resin plate precursor 26 are formed on the main surface 152 of the flat portion 153.

The positional relationship between the flat portion 153 and the protruding step portion 154 means a state where the respective main surfaces 152 thereof are not on the same plane. Cylindrical recesses 157 having a constant diameter are provided on the main surface 158 side of the protruding step portions 154. For example, the die 150 has a thickness of 150 μm. The thickness is the distance between the main surface 152 and the main surface 158.

Figure 18:
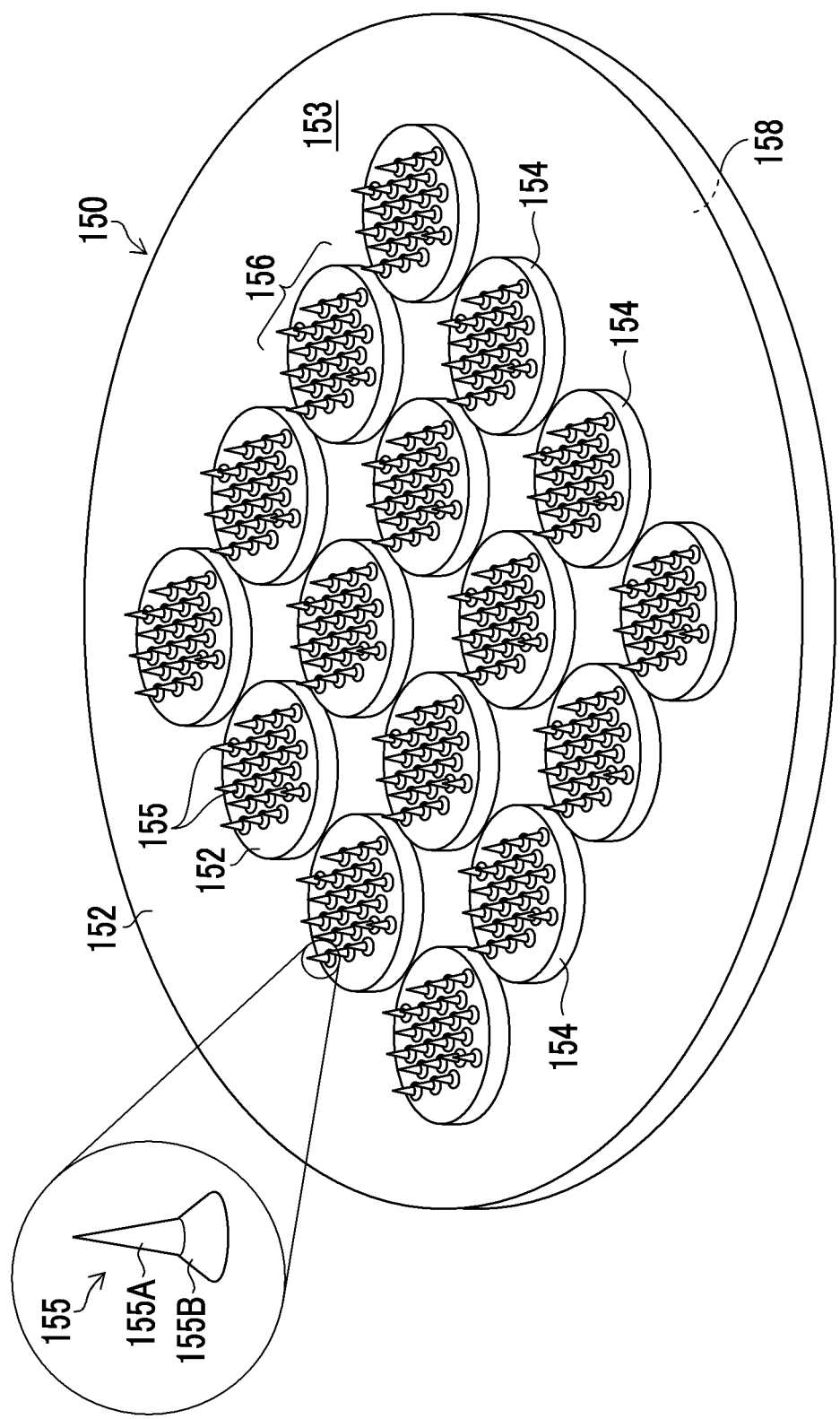
FIG. 18 is a perspective view of an electroform.

FIG. 18 is a perspective view of the die 150. As illustrated in FIG. 18, in the embodiment, the protruding pattern 156 is configured by circularly arranging the plurality of protruding portions 155 on the main surface 152 of the protruding step portion 154. Since the protruding step portion 154 and the protruding pattern 156 are formed by the thermoplastic resin plate precursor 26, the center position of the protruding step portion 154 and the center position of the protruding pattern 156 coincide with each other. The term "coincide" includes a case of perfect coincidence and a case of having an allowable deviation.

The protruding step portion 154 has a cylindrical pedestal shape having a certain height. The height of the protruding step portion 154 is the height of the recessed step portion of the thermoplastic resin plate precursor 26. The height of the protruding step portion 154 is the distance between the main surface 152 of the protruding step portion 154 and the main surface 152 of the flat portion 153 (the bottom surface of the recess 159).

The protruding portion 155 is formed by a frustum portion 155B and a tapered needle portion 155A in a direction away from the main surface 152 of the protruding step portion 154. The frustum portion 155B includes a pyramidal frustum, a conical frustum, and the like. In addition, another frustum portion may be included between the frustum portion 155B and the needle portion 155A.

The height of the protruding portion 155 is, for example, in a range of 0.1 mm to 2 mm, and preferably 0.3 mm or more and 1.5 mm or less. The height of the protruding portion 155 is the distance from the main surface 152 of the protruding step portion 154 to the tip of the protruding portion 155.

In the electroforming treatment, in order to form a metal film of a uniform thickness on the thermoplastic resin plate precursor 26, the die 150 preferably has a circular shape in a plan view. The diameter of the die 150 is preferably 200 mm to 300 mm. The circular shape is not limited to a perfect circle and may be a substantially circular shape.

Next, a mold production step using the die 150 will be described. A thermosetting resin such as an epoxy resin or a silicone resin as a mold material is prepared. In particular, it is preferable to use a silicone resin. Among silicone resins, there are one-component thermosetting silicone materials, two-component mixed curable silicone materials, UV-curable silicone materials, and the like. As a medical silicone resin, a two-component mixed curable silicone material in which a main agent and a curing agent are mixed is applied. For example, MED-6015 manufactured by Nusil can be applied as the silicone resin.

Figure 19:
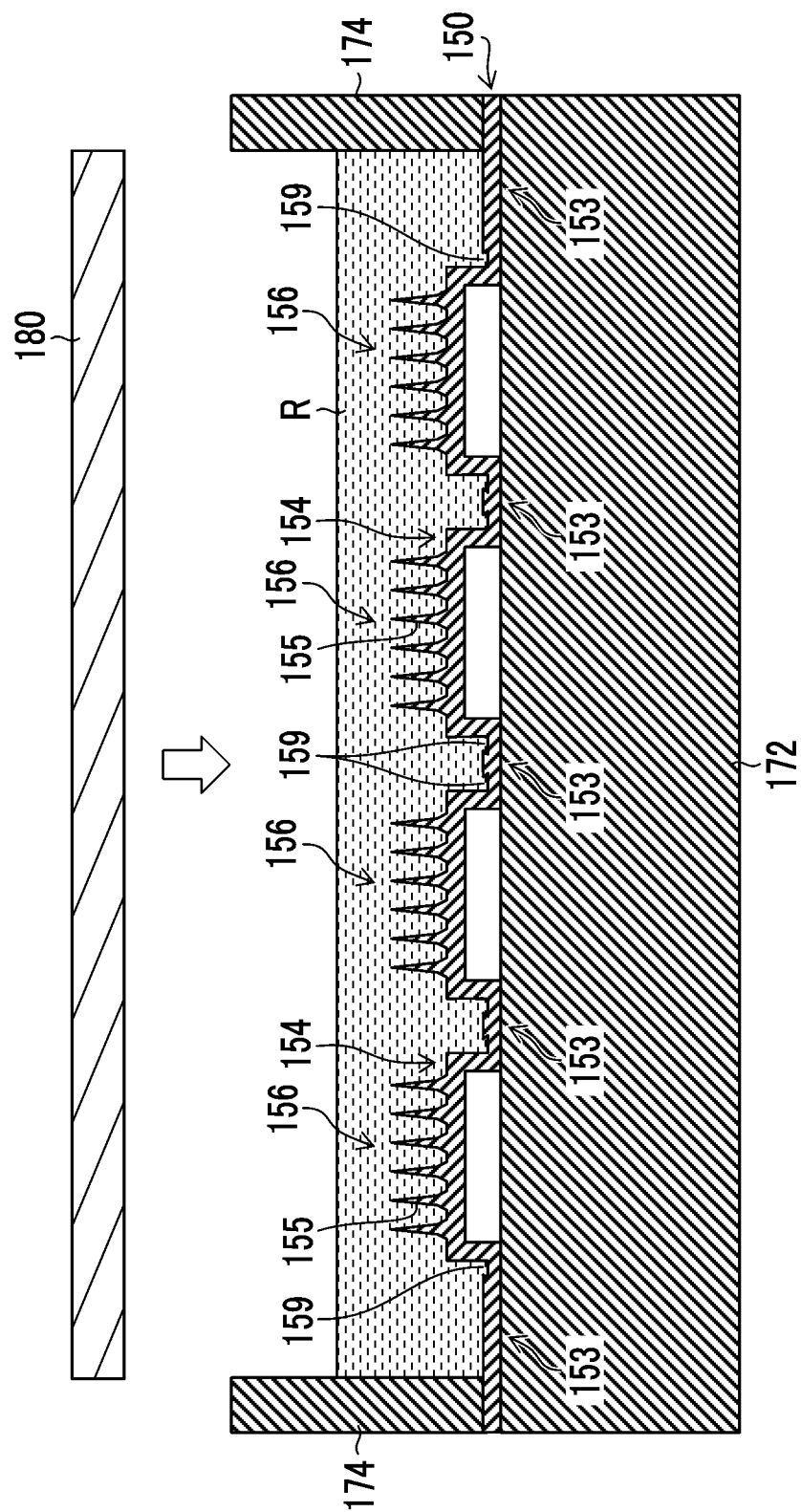
FIG. 19 is a step diagram illustrating a production method of a mold.

As illustrated in FIG. 19, in the mold production step, installation surfaces of the flat portion 153 of the die 150 and an installation pedestal 172 are arranged to face each other, and the die 150 is fixed to the installation pedestal 172. An end portion of the die 150 is pressured between a weir member 174 and the installation pedestal 172. A predetermined amount of a resin R is added dropwise from the protruding step portion 154 side of the die 150. Next, the resin R is lightly pressed by a sheet 180 made of, for example, polyethylene terephthalate (PET).

Next, in a state where the sheet 180 is brought into contact with the resin R, the sheet 180 is placed in an oven heated to 120° C. and heated for 30 minutes. The resin R is cured to produce a mold.

Figure 20:
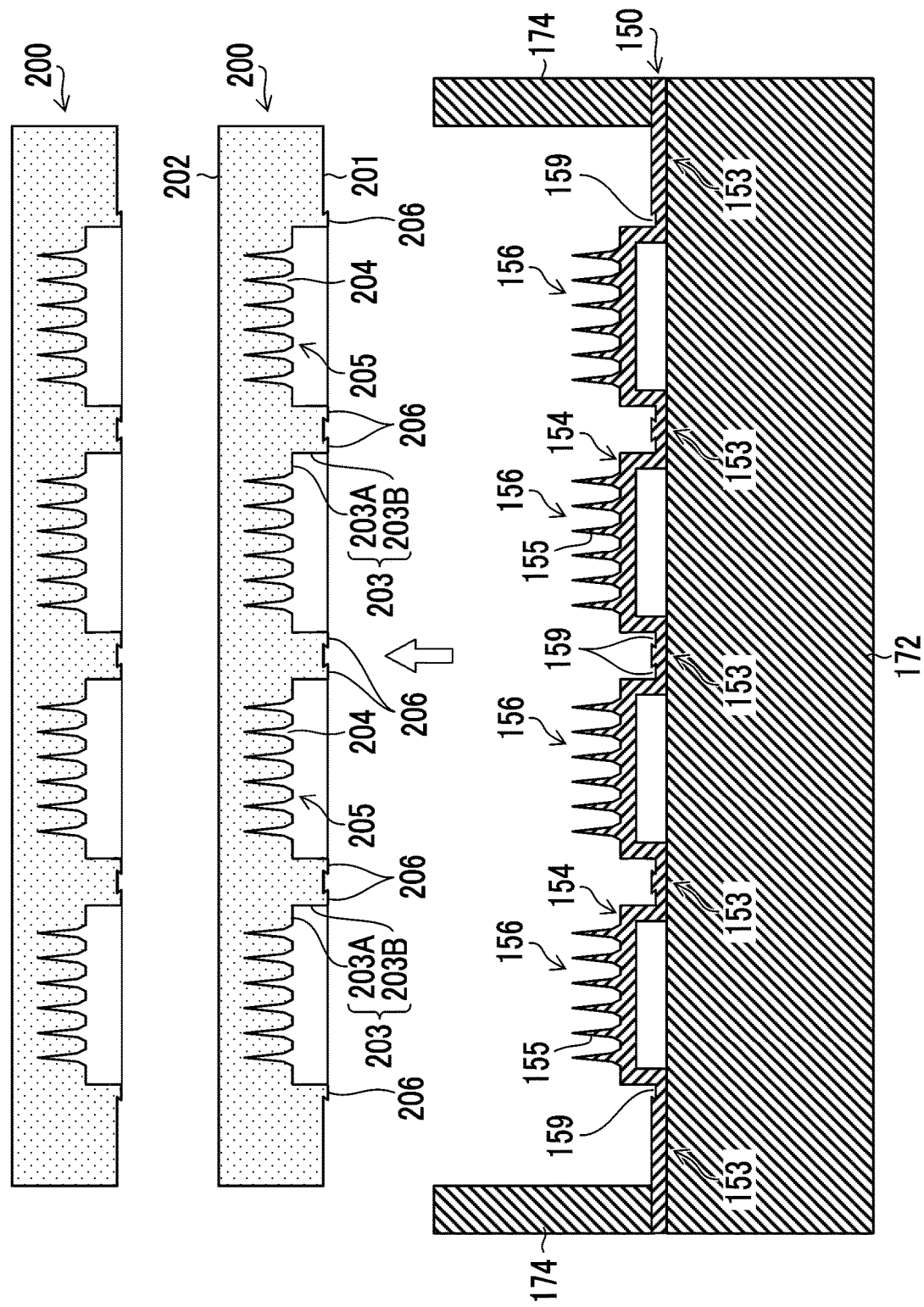
FIG. 20 is a step diagram illustrating the production method of a mold.

As illustrated in FIG. 20, a mold 200 is separated from the die 150. The inverted shape of the protruding step portions 154 of the die 150 and the protruding patterns 156 formed by the plurality of protruding portions 155 is formed in the mold 200.

The mold 200 has a main surface 201 and a main surface 202 which oppose each other. Recessed step portions 203 are formed on the main surface 201 side. The recessed step portion 203 is formed by a bottom surface 203A and a wall surface 203B. A plurality of recesses 204 are formed on the bottom surface 203A of the recessed step portion 203. In addition, on the main surface 201 side, protrusions 206 corresponding to the recesses 159 of the die 150 are formed. A recessed pattern 205 is configured by arranging a plurality of the recesses 204 on the bottom surface 203A of the recessed step portion 203. Since the recessed step portion 203 and the recessed pattern 205 are formed by the die 150, the center position of the recessed step portion 203 and the center position of the recessed pattern 205 coincide with each other. The term "coincide" includes a case of perfect coincidence and a case of having an allowable deviation.

Manufacturing Method of Pattern Sheet

Next, a method of manufacturing a pattern sheet using the mold 200 produced in the above-described production method will be described. FIGS. 21 to 24 are step diagrams for manufacturing a pattern sheet 300. A microneedle array will be described as an example of the pattern sheet 300.

Figure 21:
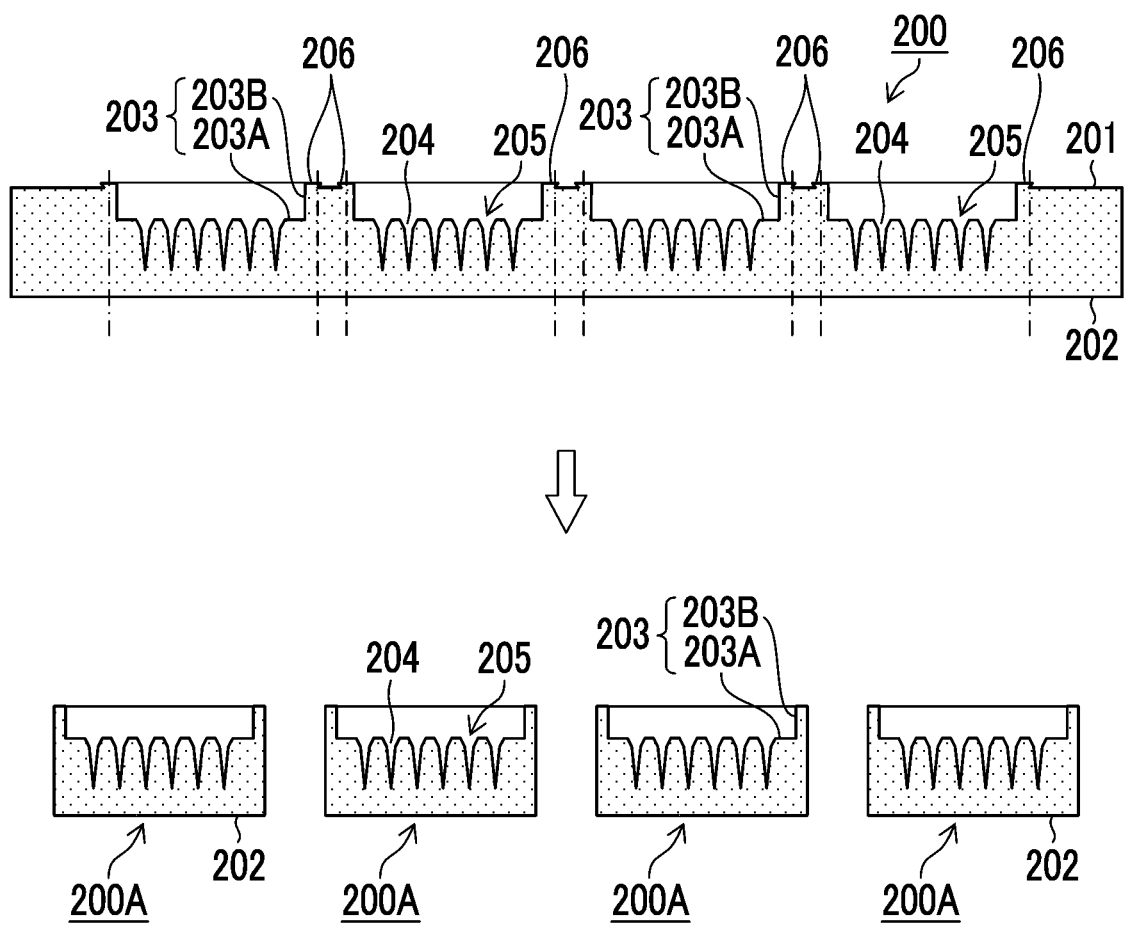
FIG. 21 is a step diagram illustrating a manufacturing method of a pattern sheet.

FIG. 21 illustrates a state where molds 200A are prepared. The molds 200A of the embodiment are produced by punching out the mold 200 manufactured by the above-described mold production method in units of the recessed step portions 203. The mold 200A has the recessed pattern 205 formed in the recessed step portion 203. In FIG. 21, the punching is performed so that the step between the protrusion 206 and the main surface 201 is not included in the mold 200A, but the position where the mold 200A is punched out is not limited. Regarding injection of a polymer solution, which will be described later, since the polymer solution is held inside the recessed step portion 203, the pattern sheet can be manufactured without being affected by the step between the protrusion 206 and the main surface 201.

The mold 200A is installed on a suction pedestal (not illustrated) in a direction in which the recessed step portion 203 is open. The mold 200A is fixed on the suction pedestal by being suctioned with a predetermined gauge pressure from the main surface 202 side of the mold 200A.

Figure 22:
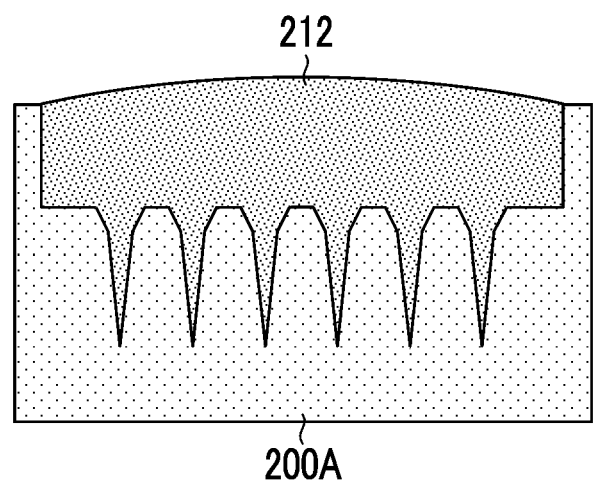
FIG. 22 is a step diagram illustrating the manufacturing method of a pattern sheet.

FIG. 22 is a diagram illustrating a supplying step of supplying a polymer solution 212 that is a liquid material to the recessed pattern 205 formed in the recessed step portion 203 of the mold 200A.

As the material of the polymer solution 212 forming the pattern sheet 300, it is preferable to use a water-soluble material. As a material of a resin polymer of the polymer solution 212 used to manufacture the pattern sheet 300, it is preferable to use a biocompatible resin. As such resins, sugars such as glucose, maltose, pullulan, sodium chondroitin sulfate, sodium hyaluronate, and hydroxyethyl starch, proteins such as gelatin, and biodegradable polymers such as polylactic acid and a lactic acid-glycolic acid copolymer are preferably used. In a case where the pattern sheet 300 is released from the mold 200A, the pattern sheet 300 can be released using a base material (not illustrated), so that such resins can be suitably used. Although a concentration varies depending on the material, it is preferable that the concentration is set so that the resin polymer is contained at 10 mass % to 50 mass % in the polymer solution 212 which does not contain a drug. A solvent used in the polymer solution 212 may be warm water or may be volatile, and alcohol such as ethanol or the like may be used. In addition, it is possible to dissolve the drug, which is supplied into the body according to the application, in the polymer solution 212. The polymer concentration of the polymer solution 212 containing the drug (the concentration of the polymer excluding the drug in a case where the drug itself is a polymer) is preferably 0 to 30 mass %.

As a method of preparing the polymer solution 212, in a case where a water-soluble polymer (such as gelatin) is used, a water-soluble powder may be dissolved in water and the drug may be added after the dissolution. Otherwise, a powder of a water-soluble polymer may be dissolved in a liquid in which the drug is dissolved. In a case where it is difficult to dissolve the polymer in water, heating may be performed for dissolution. The temperature can be appropriately selected depending on the kind of the polymer material, and it is preferable that heating is performed at a temperature of about 20° C. to 40° C. as necessary. For the solution containing the drug, the viscosity of the polymer solution 212 is preferably 200 mPas or less, and more preferably 50 mPas or less. For a solution which does not contain a drug, the viscosity is preferably 2000 mPas or less, and more preferably 500 mPas or less. By appropriately adjusting the viscosity of the polymer solution 212, the polymer solution 212 can be easily injected into the recessed patterns 205 of the mold 200A. For example, the viscosity of the polymer solution 212 can be measured with a capillary viscometer, a falling ball viscometer, a rotational viscometer, or a vibrational viscometer. It is preferable to remove gas in the polymer solution 212 by a degassing device or the like before supplying the polymer solution 212 to the mold 200A.

The drug to be contained in the polymer solution 212 is not particularly limited as long as the drug has a function of a drug. In particular, the drug is preferably selected from peptides, proteins, nucleic acids, polysaccharides, vaccines, pharmaceutical compounds that belong to a water-soluble low molecular weight compound, or cosmetic ingredients.

Examples of a method of injecting the polymer solution 212 into the mold 200A include application using a spin coater. For example, the polymer solution 212 is supplied so as to protrude from the protrusion 206 (see FIG. 21) of the mold 200A inside the recessed step portion 203. Since the mold 200A of the embodiment has the recessed step portion 203, the polymer solution 212 can be held. Since the mold 200A is suctioned from the main surface 202 in a state where the polymer solution 212 is held, the polymer solution 212 can be filled up to the recess tip of the recesses 204 forming the recessed pattern 205.

It is preferable to form a through-hole at the recess tip of the recess 204. The air in the recess 204 can escape from the through-hole. Therefore, the polymer solution 212 can easily fill the recess 204 of the mold 200A. In addition, this step is preferably performed in a decompressed state.

Figure 23:
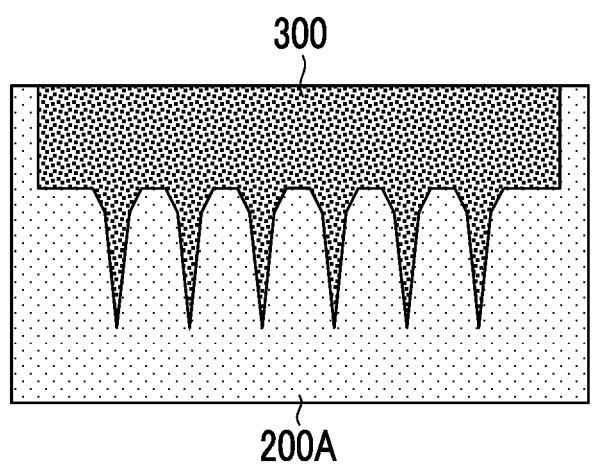
FIG. 23 is a step diagram illustrating the manufacturing method of a pattern sheet.

FIG. 23 is a diagram illustrating a step of drying and solidifying the polymer solution 212 to form the pattern sheet 300. For example, the polymer solution 212 can be dried by heating the mold 200A and blowing air to the polymer solution 212. The moisture content of the pattern sheet 300 and the like are appropriately set. In addition, as the moisture content of the pattern sheet 300 becomes too low due to the drying, it becomes difficult to peel off the pattern sheet 300. Therefore, it is preferable to keep the moisture content in a state of maintaining elasticity.

Figure 24:
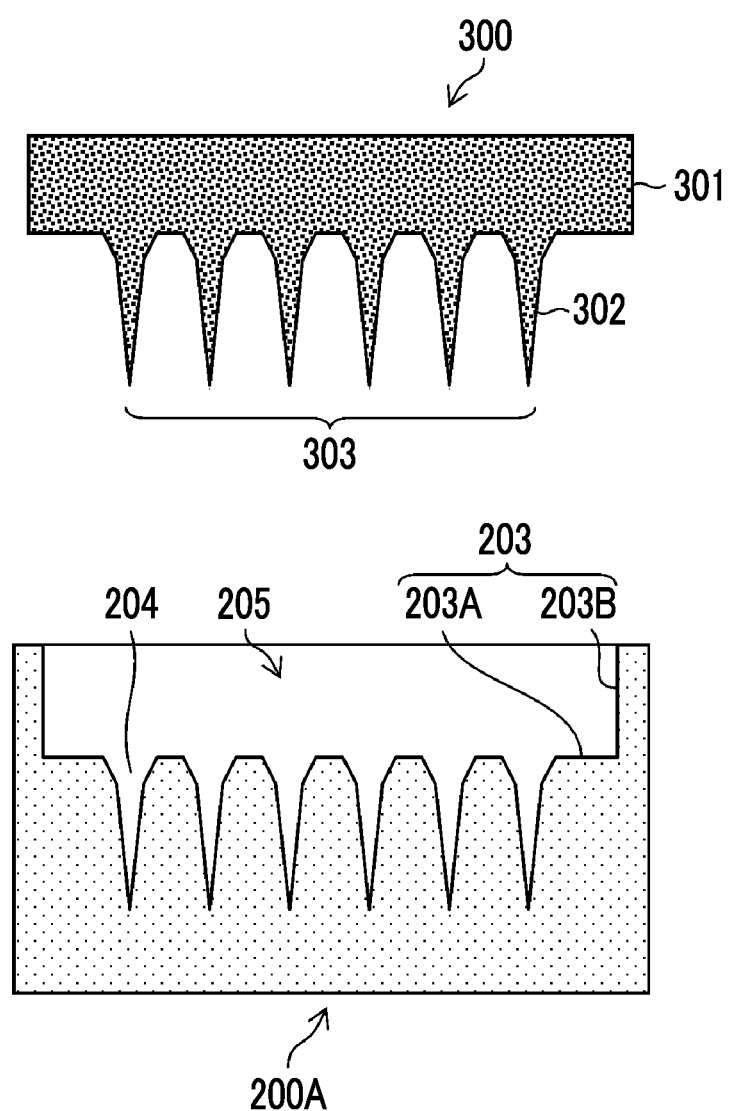
FIG. 24 is a step diagram illustrating the manufacturing method of a pattern sheet.

FIG. 24 is a diagram for describing a releasing step of releasing the pattern sheet 300 from the mold 200A. The pattern sheet 300 includes a sheet portion 301 and a plurality of protruding portions 302 formed on the sheet portion 301. A protruding pattern 303 is formed by the plurality of protruding portions 302. The protruding pattern 303 is an inverted shape of the recessed pattern 205 of the mold 200A. In the pattern sheet 300, the center position of the protruding pattern 303 and the center position of the sheet portion 301 coincide with each other. The term "coincide" includes a case of perfect coincidence and a case of having an allowable deviation. In the pattern sheet 300, since the positions of the protruding pattern 303 and the sheet portion 301 are accurately positioned, for example, in a case where the pattern sheet 300 is handled, the protruding pattern 303 can be prevented from being damaged.

As described above, in the manufacturing of the pattern sheet, in order to hold the polymer solution 212 in the recessed step portion 203, the recessed step portion 23 of the thermoplastic resin plate precursor 26 for producing the mold 200 is formed into a transfer shape of the plate precursor 10. Therefore, a pattern sheet having a stable shape can be manufactured. In addition, the pattern sheet 300 can be formed without being affected by the protrusion 206 formed outside the recessed step portion 203.

FIG. 25 is a perspective view of the pattern sheet 300. The protruding portion 302 formed on the sheet portion 301 of the pattern sheet 300 is formed by a frustum portion 302B and a tapered needle portion 302A in a direction away from the sheet portion 301. The frustum portion 302B includes a pyramidal frustum, a conical frustum, and the like. In addition, another frustum portion may be included between the frustum portion 302B and the needle portion 302A.

In the embodiment, the case where the pattern sheet 300 is produced by supplying the polymer solution 212 to the recessed step portion 203 formed in the recessed pattern 205 of the mold 200A and drying the resultant has been described above, but the production of the pattern sheet 300 is not limited thereto.

For example, a pattern sheet 300 having a two-layer structure can be manufactured by filling the recessed pattern 205 of the mold 200A with the polymer solution 212 containing the drug, drying the resultant, thereafter supplying the polymer solution 212 containing no drug to the recessed step portion 203 of the mold 200A, and drying the resultant.

In addition, there may be cases where the mold 200A is used only once and is preferably disposable. In a case where the pattern sheet 300 is used as a medicine, the pattern sheet 300 is preferably disposable in consideration of the safety of the manufactured pattern sheet 300 for the living body. By making the pattern sheet 300 disposable, there is no need to clean the mold 200A, so that the cost of the cleaning can be reduced. In particular, in a case where the pattern sheet 300 is used as a medicine, high cleaning performance is required, so that the cleaning cost is high.

The protruding pattern 303 of the manufactured pattern sheet 300 refers to a state where the plurality of protruding portions 302 are arranged in an array in a predetermined number at predetermined positions. The protruding portion 302 means a shape tapered toward the tip and includes a cone shape and a multistage cone shape. The multistage cone shape means a cone shape having sides at different angles from the bottom to the tip.

The height of the protruding portion 302 is in a range of 0.2 mm to 2 mm, preferably 0.3 mm to 1.5 mm.

According to the production method of the mold having the recessed pattern in the recessed step portion of the present invention, the shapes of the recessed pattern of the thermoplastic resin plate precursor for producing the mold and the recessed step portion on which the recessed pattern is formed can be stably formed. Therefore, in subsequent steps, an electroform and a mold can be produced stably. Moreover, by manufacturing a pattern sheet using the produced mold, work can be easily performed, and a pattern sheet having a stable shape can be manufactured.

Others

The technical scope of the present invention is not limited to the scope described in the above embodiment. The configurations and the like in the embodiments can be appropriately combined between the embodiments without departing from the gist of the present invention.

EXAMPLES

Hereinafter, the present invention will be described in more detail with reference to examples of the present invention. In addition, the material, use amount, ratio, processing content, processing procedure, and the like described in the following examples can be modified as appropriate without departing from the gist of the present invention. Therefore, the scope of the present invention should not be construed as being limited by the specific examples shown below.

Example 1

Plate Precursor

A cylindrical pedestal having a diameter $\phi$ of 17.0 mm and a height of 0.5 mm was formed at the center of a smooth aluminum alloy plate having dimensions of 6×4 cm and a thickness of t of 0.5 cm. 121 protruding portions having a needle-like structure in which a cone having a diameter $\phi$ of 0.4 mm and a height of 0.9 mm is formed on a conical frustum having a bottom diameter $\phi$ of 0.8 mm, a top diameter $\phi$ of 0.4 mm, and a height of 0.2 mm were cut at the center of the cylindrical pedestal in a circular close-packed arrangement at a pitch of 1 mm, whereby a plate precursor was obtained.

Thermoplastic Resin Plate

A plate made of LLDPE, in which 24 recessed steps having a diameter $\phi$ of 17.0 mm and a depth of 0.45 mm were provided in a close-packed arrangement on a flat plate having a diameter $\phi$ of 20 cm and a thickness of 0.3 cm, was produced by injection molding.

Lamination of Thermoplastic Resin Plate and Quartz Substrate

A quartz substrate having a $\phi$ of 20 cm and a thickness t of 0.2 mm was laminated on the surface of the thermoplastic resin plate opposite to the surface where the recessed steps were formed, via a double-sided adhesive film.

Alignment Process

The plate precursor was attached and fixed to a plate precursor stage having a Z-axis drive. The laminate obtained by laminating the thermoplastic resin plate and the quartz substrate was attached and fixed to a work stage having an X-Y-axis drive installed opposing the plate precursor (the X-axis, the Y-axis, and the Z-Axis at this time were $X_0$, $Y_0$, and $Z_0$, respectively).

(1) Plate Precursor Positional Deviation Correction

The work stage was moved to predetermined $X_{ib}$ and $Y_{ib}$ coordinates, the plate precursor was heated to 120° C., the thermoplastic resin plate was pressed in the Z-axis direction with a force of 10 N, the plate precursor was separated from the thermoplastic resin plate after being cooled and returned to $Z_0$. The inverted structure of the protruding portions having the needle-like structure was transferred to the surface ($X_{ib}$,$Y_{ib}$) of the thermoplastic resin plate.

Here, a CCD camera of an imaging device (manufactured by Keyence: image processing system XG-7000) was inserted into a fixed point ($X_c$,$Y_c$,$Z_c$), and the center ($X_{im}$, $Y_{im}$) of the inverted structure of the needle-like structure transferred to the ($X_{ib}$,$Y_{ib}$) position of the thermoplastic resin plate was detected. The positional deviation amount of the plate precursor was calculated as ($X_{ib}$–$X_{im}$) in the X direction and ($Y_{ib}$–$Y_{im}$) in the Y direction.

(2) Recessed Step Position Detection

While the CCD camera was fixed at ($X_c$,$Y_c$,$Z_c$), the X and Y positions of the thermoplastic resin plate were moved, and all the center position coordinates ($X_n$,$Y_n$) of the 24 recessed steps were detected (n=1 to 24).

Pressing Process

The work stage was moved to the recessed step ($X_1$–($X_{ib}$–$X_{im}$),$Y_1$–($Y_{ib}$–$Y_{im}$)) at n=1, the plate precursor was heated to 117° C., the thermoplastic resin plate was pressed in the Z-axis direction with a force of 80 N for a holding time t, and the plate precursor was separated from the thermoplastic resin plate after being cooled and returned to $Z_0$. The inverted structure of the needle-like structure was transferred to the center of the step ($X_1$,$Y_1$) of the thermoplastic resin plate. Furthermore, the process of similarly pressing the remaining 23 (n=2 to 24) recessed steps ($X_n$–($X_{ib}$–$X_{im}$), $Y_n$–($Y_{ib}$–$Y_{im}$)) in the Z-axis direction, separating the plate precursor from the thermoplastic resin plate after being cooled, and returning the plate precursor to $Z_0$ was repeated, whereby the inverted structure of the needle-like structure was transferred to the centers of all the 24 recessed steps. In the periphery of the recessed step portion, a protrusion was formed by the resin that had been pushed away by pressing the plate precursor.

Production of Electroform (1) Sputtering Process (Conduction Treatment)

Nickel sputtering was performed on the surface of the thermoplastic resin plate on which the inverted structure of the needle-like structure was formed at the center of the recessed step, whereby a Ni thin film was formed on the surface, the recessed steps, and the inverted structures of the thermoplastic resin plate.

(2) Electroforming Process

Next, Ni was imparted to the surface, the recessed steps, and the inverted structures of the thermoplastic resin plate subjected to the conduction treatment by the Ni thin film, by electroforming, whereby a metal body having the inverted shape of the surface of the thermoplastic resin plate was formed. Specifically, a holder to which the thermoplastic resin plate subjected to the conduction treatment was fixed was used as a cathode, a metal case holding Ni pellets was used as an anode, and the two was immersed in an electroforming liquid and energized, whereby a Ni film was formed on the surface of the thermoplastic resin plate.

In a case where the thermoplastic resin plate was peeled from the formed metal body, protruding steps were formed on the surface, such that needle-like structures were formed at the centers of the protruding steps. This was used as an electroform.

Mold Production

A mixture of a silicone resin (manufactured by Nusil.: MED-6015) main agent and a curing agent mixed in a ratio of 1:10 was prepared and added dropwise to the needle-like structure at the center of the protruding step of the electroform, and thereafter a layer was formed in a state where the mixture was lightly pressed by a PET sheet from above. The electroform was heated in an oven heated to 120° C. for 30 minutes to cure the silicone resin. In a case where the cured silicone resin was peeled from the electroform, a mold made of the silicone resin having the inverted structure of the needle-like structure at the center of the recessed step, which was the inversion of the needle-like structure formed at the center of the protruding step of the electroform, could be produced. The mold was punched with a φ20 mm circular blade so that the inverted structure of the needle-like structure was at the center, whereby 23 molds excluding a patch used for alignment were produced.

Pattern Sheet Production (1) Preparation of Base Material Solution

Hydroxypropyl cellulose (manufactured by Nippon Soda Co., Ltd.) was dissolved in water to prepare a base material solution prepared into a 30% aqueous solution. After the preparation, the resultant was exposed to a reduced pressure environment of 3 kPa for 4 minutes for degassing.

(2) Filling with Base Material Solution

The mold was installed on a horizontal suction pedestal with the surface thereof facing upward, and the mold was depressurized with a suction pressure of a gauge pressure of 90 kPa in a direction toward the rear surface of the mold to fix the mold to the suction pedestal. After the degassed base material solution was added dropwise to the recessed step formed in the mold so that the base material solution rises slightly from the upper surface of the recessed step, and left for a few minutes, and it was confirmed that the base material solution fills the inside of the inverted structure of the needle-like structure. The base material solution was prevented from flowing by the recessed steps formed in the mold.

(3) Drying of Base Material Solution

The mold was installed on a hot plate at 35° C. in an environment with a temperature of 23° C., a relative humidity of 45% RH, and a wind speed of 0.4 m/s, and left for one day to dry the base material solution. The dried base material solution became a circular sheet in a state of being in contact with the recessed steps of the mold.

(4) Peeling

In a case where the circular sheet was peeled from the mold, a needle-like structure which was the inversion of the structure of the mold was formed on the surface that had been in contact with the mold, so that a flat pattern sheet having a fine protruding pattern could be molded.

EXPLANATION OF REFERENCES 10, 310, 410, 510: plate precursor
11: pedestal
12: main surface
13: protruding portion
13A: needle portion
13B: frustum portion
14: protruding pattern
15, 315: substrate
20: thermoplastic resin plate
21: main surface
22: main surface
23: recessed step portion
23A: bottom surface
23B: wall surface
24: recess
25: recessed pattern
26: thermoplastic resin plate precursor
27: protrusion
30: quartz substrate
31: double-sided adhesive film
32: work stage
40, 440, 540: plate precursor stage
60: imaging device
61: mirror
100: cathode
101: shaft
102: cathode plate
103: conductive ring
130: electroforming apparatus
132: electroforming liquid
132A: electroforming liquid
134: electroforming tank
136: drain tank
138: Ni pellet
140: titanium case
142: drain pipe
144: supply pipe
150: die
152: main surface
153: flat portion
154: protruding step portion
155: protruding portion
155A: needle portion
155B: frustum portion
156: protruding pattern
157: recess
158: main surface
159: recess
172: installation pedestal
174: weir member
180: sheet
200: mold
200A: mold
201: main surface
202: main surface
203: recessed step portion
203A: bottom surface
203B: wall surface
204: recess
205: recessed pattern
206: protrusion
212: polymer solution
300: pattern sheet
301: sheet portion
302: protruding portion
302A: needle portion
302B: frustum portion
303: protruding pattern
316: edge portion
317, 417, 517: through-hole
418, 518: structure
419: protrusion
420: holding member
421, 521: screw
422, 522: protruding surface
523: recess
524: step portion
R: resin

What is claimed is:

1. A production method of a mold having a recessed pattern in a recessed step portion for manufacturing a pattern sheet, the production method comprising:
   a plate precursor preparation step of preparing a plate precursor having a pedestal on which a protruding pattern formed by a plurality of protruding portions is disposed;
   a resin plate preparation step of preparing a thermoplastic resin plate in which a recessed step portion having a bottom surface and a wall surface is formed on a flat surface thereof, the recessed step portion having a volume equal to or less than a total volume of the protruding pattern and the pedestal; and
   a resin plate precursor production step of producing a thermoplastic resin plate precursor, after the resin plate preparation step, the resin plate precursor production step including a positioning step of positioning the protruding pattern of the plate precursor and a center position of the recessed step portion by moving the plate precursor and the thermoplastic resin plate relative to each other, and a recessed pattern forming step of forming a recessed pattern having an inverted shape of the protruding pattern on the thermoplastic resin plate by pressing the protruding pattern of the heated plate precursor and the pedestal against the bottom surface of the recessed step portion, wherein a protrusion surrounding the recessed step portion is correspondingly formed on a main surface of the thermoplastic resin plate, thereafter cooling the plate precursor, and separating the plate precursor from the thermoplastic resin plate.

2. The production method of a mold having a recessed pattern in a recessed step portion according to claim 1,
   wherein the bottom surface of the recessed step portion has the same shape as a surface of the pedestal on which the protruding pattern is disposed, in a plan view, and
   an area of the bottom surface of the recessed step portion is equal to or less than an area of the surface of the pedestal on which the protruding pattern is disposed.

3. The production method of a mold having a recessed pattern in a recessed step portion according to claim 1,
   wherein the plate precursor comprises a substrate having a larger area than the pedestal in a plan view on a side opposite to a surface of the pedestal on which the protruding pattern is disposed, and
   a resin pushed away by pressing the pedestal against the bottom surface of the recessed step portion in the recessed pattern forming step spreads in a gap between the flat surface and the substrate.

4. The production method of a mold having a recessed pattern in a recessed step portion according to claim 3,
   wherein a surface of a protrusion formed on a flat surface of the thermoplastic resin plate precursor is continuous from the wall surface of the recessed step portion of the thermoplastic resin plate precursor, and a side surface of the protrusion on a side opposite to the recessed step portion has an inverted tapered structure which spreads from the flat surface toward the surface of the protrusion.

5. The production method of a mold having a recessed pattern in a recessed step portion according to claim 3,
   wherein an edge portion where a side surface of the pedestal and the substrate are in contact with each other has a through-hole penetrating the substrate along the side surface of the pedestal.

6. The production method of a mold having a recessed pattern in a recessed step portion according to claim 1,
   wherein a plurality of the recessed step portions are provided, and
   in the resin plate preparation step, the thermoplastic resin plate precursor is produced by repeating the positioning step and the recessed pattern forming step.

7. The production method of a mold having a recessed pattern in a recessed step portion according to claim 1, further comprising:
   a die production step of producing a die including a protruding step portion in which the protruding pattern is disposed, by an electroforming treatment using the thermoplastic resin plate precursor.

8. The production method of a mold having a recessed pattern in a recessed step portion according to claim 7, further comprising:
   a mold production step of producing a mold having an inverted shape of the protruding step portion of the die and the protruding pattern of the die using the die.

9. The production method of a mold having a recessed pattern in a recessed step portion according to claim 8,
   wherein the mold is made of a silicone resin.

10. The production method of a mold having a recessed pattern in a recessed step portion according to claim 1,
    wherein the positioning step include calculating a positional deviation amount of the plate precursor, calculating the center position of the recessed step portion of the thermoplastic resin plate, and moving the thermoplastic resin plate and the plate precursor relative to each other based on the calculated result.

11. The production method of a mold having a recessed pattern in a recessed step portion according to claim 1,
    wherein the protruding portion of the plate precursor has a frustum portion and a tapered needle portion in a direction away from the pedestal of the plate precursor.

* * * * *